US010907184B2

(12) United States Patent
Ramakrishnan et al.

(10) Patent No.: US 10,907,184 B2
(45) Date of Patent: Feb. 2, 2021

(54) AMMONIUM BASED IONIC LIQUIDS USEFUL FOR LIGNOCELLULOSIC PROCESSING

(71) Applicant: NATIONAL TECHNOLOGY & ENGINEERING SOLUTIONS OF SANDIA, LLC, Albuquerque, NM (US)

(72) Inventors: Parthasarathi Ramakrishnan, Lucknow (IN); Tanmoy Dutta, Berkeley, CA (US); Blake Simmons, San Francisco, CA (US); Seema Singh, Clarksburg, MD (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/778,924

(22) PCT Filed: Nov. 23, 2016

(86) PCT No.: PCT/US2016/063694
§ 371 (c)(1),
(2) Date: May 24, 2018

(87) PCT Pub. No.: WO2017/091781
PCT Pub. Date: Jun. 1, 2017

(65) Prior Publication Data
US 2018/0355392 A1    Dec. 13, 2018

Related U.S. Application Data

(60) Provisional application No. 62/259,217, filed on Nov. 24, 2015.

(51) Int. Cl.
C12P 19/00 (2006.01)
C12P 19/04 (2006.01)
(Continued)

(52) U.S. Cl.
CPC .......... C12P 19/04 (2013.01); C08B 37/0057 (2013.01); C08H 8/00 (2013.01);
(Continued)

(58) Field of Classification Search
None
See application file for complete search history.

(56) References Cited

U.S. PATENT DOCUMENTS

2010/0081798 A1* 4/2010 Balensiefer ............. C12P 19/02
530/500
2011/0251377 A1* 10/2011 Rahman ................. D21C 3/006
530/500
(Continued)

FOREIGN PATENT DOCUMENTS

WO    2006/034590 A1    4/2006
WO    2012/174459 A2    12/2012
(Continued)

OTHER PUBLICATIONS

Brandt, et al., "Deconstruction of lignocellulosic biomass with ionic liquids," Green Chemistry (2013), 15:3, pp. 550-583.
(Continued)

Primary Examiner — Stefanie J Cohen
(74) Attorney, Agent, or Firm — Kilpatrick Townsend & Stockton LLP

(57) ABSTRACT

Methods and compositions are provided for ionic liquid processing of biomass.

15 Claims, 11 Drawing Sheets

[TBA][OH]— dilignol $[C_2C_1Im]$ [OAc]— dilignol

(51) Int. Cl.
   *C12P 19/02* (2006.01)
   *C13K 1/02* (2006.01)
   *C08H 8/00* (2010.01)
   *C08B 37/00* (2006.01)
   *C13K 13/00* (2006.01)
(52) U.S. Cl.
   CPC ............... *C12P 19/02* (2013.01); *C13K 1/02* (2013.01); *C12P 2201/00* (2013.01); *C12P 2203/00* (2013.01); *C13K 13/002* (2013.01)

(56) References Cited

U.S. PATENT DOCUMENTS

| | | | | |
|---|---|---|---|---|
| 2012/0301948 | A1* | 11/2012 | Brennan | C07H 1/08 435/243 |
| 2012/0315695 | A1 | 12/2012 | Brennan et al. | |
| 2013/0183739 | A1* | 7/2013 | Singh | C08B 37/0003 435/209 |
| 2014/0005415 | A1* | 1/2014 | Sun | C01B 33/40 549/230 |
| 2014/0326422 | A1* | 11/2014 | Fallon | D21C 3/20 162/16 |

FOREIGN PATENT DOCUMENTS

| | | |
|---|---|---|
| WO | 2013/096369 A1 | 6/2013 |
| WO | 2014/138100 A1 | 9/2014 |
| WO | 2015/079262 A1 | 6/2015 |

OTHER PUBLICATIONS

Sathisuksanoh, et al., "New lignocellulose pretreatments using cellulose solvents: a review," Journal of Chemical Technology and Biotechnology (2013), 88:2, pp. 169-180.

Shemfe, et al., "Techno-economic performance analysis of biofuel production and miniature electric power generation from biomass fast pyrolysis and bio-oil upgrading," Fuel (2015) 143, pp. 361-372.

Parthasarathi, et al., "Activation of lignocellulosic biomass for higher sugar yields using aqueous ionic liquid at low severity process conditions," Biotechnology for Biofuels (2016), 9:160, pp. 1-13.

Zhong, et al. "Wheat straw cellulose dissolution and isolation by tetra-n-butylammonium hydroxide," Carbohydrate Polymers, 94 (2013), pp. 38-45.

* cited by examiner

[C₂C₁Im][OAc]—dilignol

[TBA][OH]—dilignol

AMMONIUM BASED IONIC LIQUIDS USEFUL FOR LIGNOCELLULOSIC PROCESSING

CROSS-REFERENCES TO RELATED APPLICATIONS

This application claims the benefit of priority to U.S. Provisional Appl. No. 62/259,217, filed on Nov. 24, 2015, the contents of which are hereby incorporated by reference in the entirety and for all purposes.

STATEMENT AS TO RIGHTS TO INVENTIONS MADE UNDER FEDERALLY SPONSORED RESEARCH AND DEVELOPMENT

The invention was made with government support under Contract No. DE-AC02-05CH11231 awarded by the U.S. Department of Energy. The government has certain rights in the invention.

BACKGROUND OF THE INVENTION

Lignocellulosic biomass is an abundant renewable resource primarily composed of cellulose, lignin, and hemicellulose that form a complex composite structure. [Canadell J G, Schulze E D, *Nat Commun.* 2014; 5: 1-12; Schubert C., *Nat Biotech.* 2006; 24(7): 777-784; Tanger P et al., *Frontiers in Plant Science.* 2013; 4(218): 1-20; Wyman C E. Aqueous pretreatment of plant biomass for biological and chemical conversion to fuels and chemicals. John Wiley & Sons. 2013]. The recalcitrance of this complex composite poses a significant barrier to economical, chemical, or biological conversion technologies that can convert the fermentable sugars present in lignocellulose into advanced biofuels and renewable chemicals. [Himmel M E, et al, *Science.* 2007; 315(5813): 804-807].

Several physical and/or chemical pretreatment processes have been implemented to reduce the recalcitrance of lignocellulosic materials and improve their utilization. [Wyman C E, et al., *Bioresource Technology.* 2005; 96(18): 1959-1966; Kumar P, Barrett D M et al., *Industrial & Engineering Chemistry Research.* 2009; 48(8): 3713-3729; Yang B, Wyman C E, *Biofuels, Bioproducts and Biorefining.* 2008: 2(1): 26-40]. Conventional pretreatments, such as those that use concentrated or dilute acids and bases, are only effective in producing a substrate capable of generating high fermentable sugar yields by using severe process conditions (~120-200° C.).

After pretreatment, the recovered substrate is saccharified using enzyme mixtures at 40-80° C. There is an intricate interplay between the type of pretreatment and fermentable sugar yields achieved (FIG. 1). [Wyman C E, et al., *Bioresource Technology.* 2005; 96(18): 1959-1966; Balan V et al., In: Mielenz J R (ed). *Biofuels*, vol. 581. Humana Press, 2009, pp 61-77; Li C, et al., *Bioresource technology.* 2010; 101(13): 4900-4906; Sendich E, et al., *Bioresource Technology.* 2008; 99(17): 8429-8435; Singh S, Simmons B A, Vogel K P, *Biotechnology and Bioengineering.* 2009; 104 (1): 68-75; Tao L, et al., *Bioresource Technology.* 2011; 102(24): 11105-11114; Uppugundla N, et al., *Biotechnol. Biofuels.* 2014; 7: 72; Dutta T, et al., *Ionic Liquids in the Biorefinery Concept: Challenges and Perspectives.* The Royal Society of Chemistry, 2016, pp 65-94].

These higher temperature process technologies increase the energy required and thereby increase production costs. [Kumar P, Barrett D M et al., *Industrial & Engineering Chemistry Research.* 2009; 48(8): 3713-3729]. Generally, temperature of pretreatment process has been set around the range of the glass transition temperature of lignin thereby impacting the physicochemical properties of lignin and cellulose, [Li W, et al., *Green Chemistry.* 2011; 13(8): 2038-2047] hemicellulose hydrolysis, [Tsao G T, Recent progress in bioconversion of lignocellulosics, vol. 65. Springer Science & Business Media, 1999] and cellulose digestion [Debzi E et al., *Macromoleculcules.* 1991; 24(26): 6816-6822].

Certain ionic liquids (ILs) are able to dissolve either lignocellulosic materials or one of its main constituents such as cellulose, hemicellulose, or lignin. [Brandt A et al., *Green Chemistry.* 2013; 15(3): 550-583]. The IL 1-ethyl-3-methylimidazolium acetate ([$C_2C_1$Im][OAc]) based IL pretreatment process typically requires temperatures above 140° C. for 3 hrs reaction time in order to be effective and typically use pure IL as the pretreatment solvent. [Li C, et al., *Bioresource technology.* 2010; 101(13): 4900-4906; Singh S, Simmons B A, Vogel K P, *Biotechnology and Bioengineering.* 2009; 104(1): 68-75; Shi J, et al., *Biofuels.* 2013; 4(1): 63-72; Sun N, et al., *Green Chemistry.* 2014; 16(5): 2546-2557; Singh S, Simmons B A, *Aqueous Pretreatment of Plant Biomass for Biological and Chemical Conversion to Fuels and Chemicals.* John Wiley & Sons, Ltd, 2013, pp 223-238]. Thus, there remains a need for lower temperature processes for pre-treatment, saccharification, and/or fermentation.

BRIEF SUMMARY OF THE INVENTION

In one aspect, the present invention provides a method for treating a biomass comprising polysaccharide and lignin, the method comprising:
(i) providing a pre-treatment mixture comprising the biomass at a concentration of at least about 5% (w/w), an ionic liquid or mixture of ionic liquids at a concentration of at least about 40% w/w, and optionally water, wherein the ionic liquid or mixture thereof comprises:
a) a quaternary ammonium cation comprising four alkyl groups covalently linked to the ammonium cation, wherein each of the four alkyl groups is independently selected from the group consisting of $C_1$-$C_6$ alkyl; and
b) an anion selected from the group consisting of $OH^-$, $HSO_4^-$, $H_2PO_4^-$, $PO_4^-$, lysinate, $HCO_3^-$, and $Cl^-$;
(ii) maintaining the mixture under pre-treatment conditions sufficient to dissolve at least a portion of the polysaccharide present in the biomass, wherein the pre-treatment conditions comprise a temperature of at least about 20° C. and less than about 100° C. for a duration of at least about 0.5 hours.

In some embodiments, the pre-treatment mixture comprises an ionic liquid comprising a tetrabutylammonium (TBA) cation. In some embodiments, the pre-treatment mixture comprises an ionic liquid comprising an $OH^-$ anion. In some embodiments, the pre-treatment mixture comprises a single ionic liquid, wherein the single ionic liquid in the pre-treatment mixture comprises a tetrabutylammonium (TBA) cation. In some embodiments, the pre-treatment mixture comprises an ionic liquid solution consisting of water and a single ionic liquid, wherein the single ionic liquid in the ionic liquid solution comprises a tetrabutylammonium (TBA) cation or consists of TBAOH.

In some embodiments, the pre-treatment mixture comprises a single ionic liquid, wherein the single ionic liquid in the pre-treatment mixture comprises the $OH^-$ anion. In some embodiments, the pre-treatment mixture comprises an ionic liquid solution consisting of water and a single ionic liquid, wherein the single ionic liquid in the ionic liquid solution comprises the OH⁻ anion or consists of TBAOH. In some embodiments, the pre-treatment mixture comprises a single ionic liquid, wherein the single ionic liquid in the pre-treatment mixture comprises TBAOH. In some embodiments, the pre-treatment mixture comprises an ionic liquid solution consisting of a single ionic liquid and water, wherein the single ionic liquid in the ionic liquid solution comprises or consists of TBAOH.

In some embodiments, the pre-treatment mixture comprises the mixture of ionic liquids, each independently comprising the quaternary ammonium cation comprising four alkyl groups covalently linked to the ammonium cation, wherein each of the four alkyl groups is independently selected from the group consisting of $C_1$-$C_6$ alkyl. In some embodiments, the mixture of ionic liquids in the pre-treatment mixture comprises at least two different anions selected from the group consisting of OH⁻, $HSO_4^-$, $H_2PO_4^-$, $PO_4^-$, lysinate, $HCO_3^-$, and Cl⁻, and the quaternary ammonium cation comprising four alkyl groups covalently linked to the ammonium cation, wherein each of the four alkyl groups is independently selected from the group consisting of $C_1$-$C_6$ alkyl. In some embodiments, the mixture of ionic liquids in the pre-treatment mixture comprises at least two different anions selected from the group consisting of OH⁻, $HSO_4^-$, $H_2PO_4^-$, $PO_4^-$, lysinate, $HCO_3^-$, and Cl⁻, and tetrabutylammonium (TBA).

In some embodiments, the pre-treatment conditions comprise conditions sufficient to remove at least 50% of the lignin present in the biomass. In some embodiments, the pre-treatment conditions comprise a temperature of at least about 25° C. and less than about 75° C. In some embodiments, the pre-treatment conditions comprise a temperature of at least about 30° C. and less than about 60° C. In some embodiments, the pre-treatment conditions comprise maintaining the temperature of the pre-treatment mixture with less than about 40 MT/hr of steam to process 2000 MT/day of dry biomass. In some embodiments, the pre-treatment conditions comprise maintaining the temperature of the pre-treatment mixture at between about 40 and 60° C. with between about 10 and about 40 MT/hr of steam to process 2000 MT/day of dry biomass.

In some embodiments, the pH of the pre-treatment mixture is from about 7.5 to about 14. In some embodiments, the pH of the pre-treatment mixture is from about 8 to about 13. In some embodiments, the pH of the pre-treatment mixture is from about 9 to about 12. In some embodiments, the ionic liquid or mixture of ionic liquids (e.g., in the pre-treatment mixture and/or in the ionic liquid solution of the pre-treatment mixture) is at a concentration of between about 40% and about 90% w/w.

In some embodiments, providing the pre-treatment mixture comprises mechanically reducing the biomass to a smaller particle size. In some embodiments, mechanically reducing comprises milling the biomass. In some embodiments, after (ii), the method further comprises: (iii) diluting the pre-treatment mixture with a polar solvent. In some embodiments, the polar solvent is selected from the group consisting of water, methanol, ethanol, propanol, isopropanol, butanol, pentanol, hexanol, heptanol, octonol, and isooctonol. In some embodiments, the polar solvent is water. In some embodiments, the method further comprises diluting the pre-treatment mixture with at least two different polar solvents. In some embodiments, the method comprises diluting the pre-treatment mixture with from about 2 volumes of polar solvent to about 10 volumes of polar solvent.

In some embodiments, step (iii) further comprises reducing the pH of the pre-treatment mixture with an acid, and after diluting the pre-treatment mixture, the method comprises: (iv) contacting the diluted pre-treated mixture with a glycoside hydrolase under conditions sufficient to hydrolyze at least a portion of the glucan, thereby forming a sugar composition, wherein the sugar composition comprises at least one monosaccharide or oligosaccharide. In some embodiments, after diluting the pre-treatment mixture, the method comprises: (iv) collecting pre-treated biomass solids from the mixture, wherein the pre-treated biomass solids comprise at least about 50% of glucan present in the biomass provided in the pre-treatment mixture. In some embodiments, after diluting the pre-treatment mixture, the method comprises: (iv) collecting pre-treated biomass solids from the mixture, wherein the pre-treated biomass solids comprise from about 90% to about 95% of glucan present in the biomass provided in the pre-treatment mixture.

In some embodiments, collecting the pre-treated biomass solids comprises filtering or centrifugation. In some embodiments, collecting the pre-treated biomass solids comprises washing away residual ionic liquid with a polar solvent. In some embodiments, the method further comprises: (v) contacting the pre-treated biomass solids with a glycoside hydrolase under conditions sufficient to hydrolyze at least a portion of the glucan, thereby forming a sugar composition, wherein the sugar composition comprises at least one monosaccharide or oligosaccharide. In some embodiments, the method comprises reducing the pH of the pre-treatment mixture or of a slurry containing the biomass solids to adjust the pH of the mixture to a pH of from about 4.8 to about 5.2, or from about 5.2 to about 6.2. In some embodiments, the glycoside hydrolase comprises a cellulase. In some embodiments, the glycoside hydrolase is selected from the group consisting of an endoglucanase, an exoglucanase, a β-glucosidase, a xylanase, and mixtures thereof.

In some embodiments, the method comprises contacting the pre-treated biomass solids or diluted pre-treatment mixture with the cellulase under conditions sufficient to release at least about 70% of glucose monomers present in the biomass provided in the pre-treatment mixture. In some embodiments, the method comprises contacting the pre-treated biomass solids or diluted pre-treatment mixture with the cellulase under conditions sufficient to release at least about 90% of glucose monomers present in the biomass provided in the pre-treatment mixture.

In a second aspect, the present invention provides a method for preparing a sugar composition comprising:
  (i) providing a pre-treatment mixture comprising biomass at a concentration of at least about 5% (w/w), an ionic liquid or mixture of ionic liquids at a concentration of at least about 40% w/w, and optionally water, wherein the biomass comprises lignin and polysaccharide, and wherein the ionic liquid or mixture thereof comprises:
    a) a tetrabutylammonium cation; and
    b) a hydroxide anion (OH⁻), a bicarbonate anion ($HCO_3^-$), and a chloride anion (Cl⁻);
  (ii) maintaining the mixture under pre-treatment conditions sufficient to dissolve at least a portion of the polysaccharide present in the biomass, wherein the pre-treatment conditions comprise a temperature of at least about 15° C. and less than about 65° C. for a duration of at least about 0.5 hours;
  (iii) diluting the pre-treatment mixture with a polar solvent to form a diluted pre-treatment mixture, and optionally collecting pre-treated biomass solids from the diluted pre-treatment mixture; and (iv) contacting the pre-treated biomass solids with a glycoside hydrolase under conditions sufficient to hydrolyze at least a portion of the polysaccharide, thereby forming a sugar composition, wherein the sugar composition comprises at least one monosaccharide or oligosaccharide.

In some embodiments, the method comprises reducing the pH and the temperature of the pre-treatment mixture or the diluted pre-treatment mixture and contacting the (e.g., diluted) pre-treatment mixture with the glycoside hydrolase. In some embodiments, the pH of the pre-treatment mixture is from about 7.5 to about 14. In some embodiments, the pH of the pre-treatment mixture is from about 8 to about 13. In some embodiments, the pH of the pre-treatment mixture is from about 9 to about 12. In some embodiments, the method comprises adjusting a pH of a mixture comprising the pre-treated biomass solids (e.g., the pre-treatment mixture or diluted pre-treatment mixture or a mixture containing pre-treated biomass solids collected from a pre-treatment mixture) to a pH of from about 4.8 to about 5.2, or from about 5.2 to about 6.2.

In a third aspect, the present invention provides a method for converting a sugar composition to a fermentation product, the method comprising fermenting a mixture containing a sugar composition prepared according to one or more of the foregoing methods.

DETAILED DESCRIPTION OF THE INVENTION

I. Introduction

Figure 1:
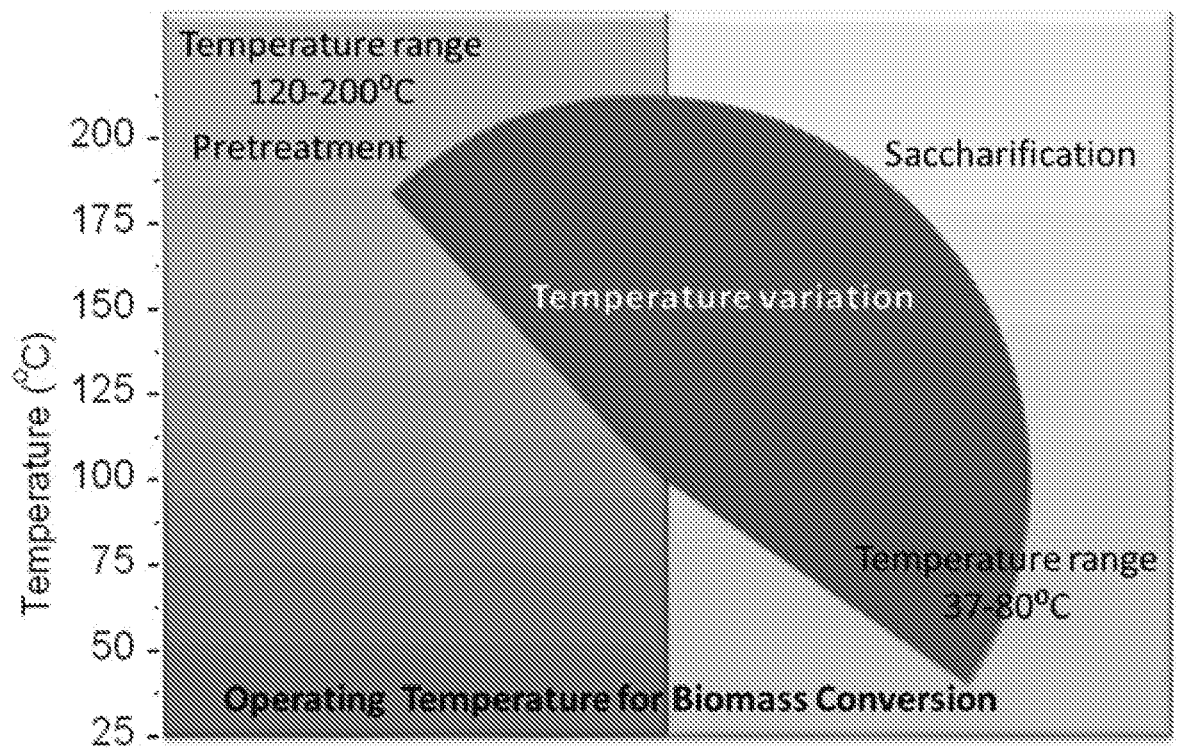
FIG. 1. Temperature variations in a typical biomass pre-treatment and saccharification processes.

The development of cost-effective methods conversion of biomass (e.g., lignocellulosic biomass) into useful fermentation products is an important area of research. Such methods can be used to generate pharmaceuticals or intermediates in the production of pharmaceuticals, cosmetics, food ingredients, biofuels, or combinations thereof. Typically, the biomass must be mechanically and/or chemically pre-treated to allow efficient hydrolysis and/or fermentation. Pre-treatment processes can be require large amounts of energy and time. Moreover, pre-treatment chemicals can be expensive to produce, recycle, and/or dispose. Pre-treatment with ionic liquids is thought to be a promising avenue for addressing these issues. However, the ionic liquids themselves are typically high in cost, and high temperature and/or pressures can still be necessary to achieve sufficient levels of pre-treatment. The present inventors have surprisingly discovered that ionic liquids containing a quaternary ammonium cation and an anion are surprisingly effective at biomass pre-treatment when used in an aqueous mixture at relatively low concentrations and under low temperature and/or pressure conditions.

II. Definitions

As used herein, the term "sugar composition" refers to a mixture containing one or more monosaccharides, oligosaccharides, or combinations thereof. Sugar compositions prepared according to the methods of the present invention by contacting pre-treated biomass with one or more glycoside hydrolases are also referred to as "hydrolysates" in the present application.

As used herein, the term "monosaccharide" refers to a sugar having a five-membered carbon backbone (i.e., a pentose) or a six-membered carbon backbone (i.e., a hexose). Examples of monosaccharides include, but are not limited to, glucose, ribose, fucose, xylose, arabinose, galactose, mannose, glucuronic acid, and iduronic acid. Monosaccharides also include pentoses and hexoses substituted with hydroxy groups, oxo groups, amino groups, acetylamino groups, and other functional groups.

As used herein, the term "oligosaccharide" refers to a compound containing at least two sugars covalently linked together. Oligosaccharides include disaccharides, trisaccharides, tetrasaccharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent sugars (i.e., a 1-3 linkage), the 1-carbon (the anomeric carbon) and the 6-carbon of adjacent sugars (i.e., a 1-6 linkage), or the 1-carbon (the anomeric carbon) and the 2-carbon of adjacent sugars (i.e., a 1-2 linkage). Other linkages can be present in the oligosaccharide, depending on the particular sugar subunits present. Those of skill in the art will appreciate that a sugar can be linked within an oligosaccharide such that the glycosidic bond at the anomeric carbon is in the α- or β-configuration.

As used herein, the term "polysaccharide" generally refers to a compound containing 10 or more sugars linked together as described for oligosaccharides.

As used herein, the term "biomass" and "polysaccharide biomass" are used interchangeably to refer to plant-based material that includes a plurality of components such as lignin, cellulose, and hemicellulose. Sources of biomass includes trees, shrubs, grasses, wheat, wheat straw, sugar cane bagasse, corn, corn husks, corn kernel including fiber from kernels, products and by-products from milling of grains such as corn, rice, wheat, and barley, as well as municipal solid waste, waste paper, and yard waste. Biomass sources can also include herbaceous material, agricultural residues, forestry residues, and paper mill residues. Additional examples include branches, bushes, canes, corn and corn husks, energy crops, forests, fruits, flowers, grains, grasses, herbaceous crops, leaves, bark, needles, logs, roots, saplings, short rotation woody crops, shrubs, switchgrasses, trees, vegetables, fruit peels, vines, sugar beet pulp, wheat midlings, oat hulls, hard and soft woods, organic waste materials generated from agricultural processes including farming and forestry activities, or mixtures thereof. Biomass generally can contain (but need not contain) xylan, protein, and/or other carbohydrates, such as starch.

As used herein, the term "lignocellulosic biomass" refers to natural and/or synthetic materials containing lignin, cellulose, and/or hemicellulose. Generally, these materials also contain (but need not contain) xylan, protein, and/or other carbohydrates, such as starch.

As used herein, the term "cellulose" refers to refers to a homopolymer of β(1→4) linked D-glucose units that form a linear chain. Cellulose can contain several hundred to several thousand or more glucose units, making cellulose a polysaccharide.

As used herein, the term "hemicellulose" refers to a heteropolymer containing different saccharide units, including but not limited to, xylose, mannose, galactose, rhamnose and arabinose. Hemicellulose forms a branched polymer with several hundred to several thousand sugar units. Hemicellulose can include both pentose and hexose sugars.

As use herein, the term "lignin" refers to a phenylpropane polymer of monolignol monomers (p-coumaryl alcohol, coniferyl alcohol, and sinapyl alcohol) found as an integral part of the secondary cell walls of plants and certain types of algae As used herein, the term "ionic liquid" refers to an organic salt that is a liquid at room temperature rather than a solid or crystalline substance. Ionic liquids typically exhibit a number of advantageous properties, including low volatility, thermal stability, and the ability to dissolve a wide range of solutes under mild conditions.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. An "alkane" refers to the parent compound of the alkyl radicals described herein.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. An "alkene" refers to the parent compound of the alkenyl radicals described herein.

As used herein, the term "dicarboxylic acid" refers to and alkane or alkene having two carboxy moieties (i.e., —COOH groups). As used herein, the term "dicarboxylic acid anion" refers to a dicarboxylic acid wherein one or two of the carboxy moieties is deprotonated (i.e., present as a —COO⁻ anion). Dicarboxylic acid anions are generally bound to cations in an ionic liquid via electrostatic interaction.

As used herein, the term "cation" refers to a positively charged molecule that pairs with an anion in an ionic liquid via electrostatic interaction. Examples of cations suitable for inclusion in ionic liquids include, but are not limited to, ammonium, imidazolium, pyridinium, sulfonium, and phosphonium cations.

An exemplary cation suitable for inclusion in an ionic liquid is an ammonium cation such as a quaternary ammonium cation. "Quaternary ammonium" refers to ammonium compounds of general formula $^+N—(R)_4$ wherein R is an alkyl or an aryl group, an exemplary quaternary ammonium compound is tetrabutylammonium.

As used herein, the term "anion" refers to a negatively charged molecule that pairs with a cation in an ionic liquid via electrostatic interaction. Examples of anions suitable for inclusion in ionic liquids include, but are not limited to, carboxylic acid anion, dicarboxylic acid anion, lysinate, hydroxide, bisulfate, sulfate, hydrogen phosphate, dihydrogen phosphate, bicarbonate, and chloride anions. An exemplary cation anion pair forming an ionic liquid is tetrabutylammonium hydroxide (TBAOH).

As used herein, the term "pH" refers to refers to a measurement of the concentration of hydrogen ions in a mixture such as an aqueous solution. pH is expressed as the decimal logarithm (i.e., $\log_{10}$) of the reciprocal of the hydrogen ion concentration in the mixture. The pH of a mixture can be determined using a number of known techniques. One of skill in the art will know how to adjust the pH of a mixture by adding acids and/or bases to the mixture.

As used herein, the term "acid" refers to a substance that is capable of donating a proton (i.e., a hydrogen cation) to form a conjugate base of the acid. Examples of acids include, but are not limited to, hydrochloric acid, sulfuric acid, acetic acid, and formic acid.

As used herein, the term "base" refers to a substance that is capable of accepting a proton (i.e., a hydrogen cation) to form a conjugate acid of the base. Examples of bases include, but are not limited to, sodium hydroxide, potassium hydroxide, sodium bicarbonate, and potassium carbonate.

As used herein, the terms "dissolve" and "dissolution" refer to the solvation of a solute with a solvent to form a solution. More particularly, dissolution refers to the partial or complete solubilization of biomass in an ionic liquid or an ionic liquid solution. In the methods of the invention, dissolution of lignocellulosic biomass can include partial or complete disruption of intra- and intermolecular hydrogen bonds present in cellulose polymer chains, partial or complete disruption of interactions between cellulose and hemicellulose, and partial or complete solubilization of lignin.

The terms "hydrolyze," "hydrolysis," and "saccharification," when used herein with respect to polysaccharide chemistry, refer to the cleavage of one or more glycosidic bonds in an oligosaccharide or a polysaccharide by water. The hydrolysis is typically catalyzed by an enzyme such as a glycoside hydrolase. Hydrolysis can also be promoted by addition of a catalyst such as an acid or base.

As used herein, the term "glycoside hydrolase" refers to an enzyme that catalyzes the cleavage of the glycosidic linkage in oligosaccharides or polysaccharides by water to release smaller sugars.

As used herein, the terms "fermenting" and "fermentation" refer to a metabolic process performed by an organism that converts one substrate to another, such as when an organism utilizes glucose and converts it to ethanol or propionic acid. In the present invention "fermentation" is typically used broadly to refer to the conversion of simple sugars to a desired product.

The terms "about" and "around," as used herein to modify a numerical value, indicate a close range surrounding that explicit value. If "X" were the value, "about X" or "around X" would indicate a value from 0.9X to 1.1X. "About X" thus includes, for example, a value from 0.95X to 1.05X. Any reference to "about X" or "around X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.07X, 1.08X, 1.09X, and 1.10X. Accordingly, "about X" and "around X" are intended to teach and provide written description support for a claim limitation of, e.g., "0.98X."

III. Methods

In one aspect, the present invention provides a method for pre-treating biomass with an ionic liquid or mixture of ionic liquids. In typical embodiments, a method of the invention, includes:
(i) providing a pre-treatment mixture comprising the biomass at a concentration of at least about 5% (w/w), an ionic liquid or mixture of ionic liquids at a concentration of at least about 40% w/w, and optionally water, wherein the ionic liquid or mixture thereof comprises:
  a) a quaternary ammonium cation comprising four alkyl groups covalently linked to the ammonium cation, wherein each of the four alkyl groups is independently selected from the group consisting of $C_1$-$C_6$ alkyl; and
  b) an anion selected from the group consisting of $OH^-$, $HSO_4^-$, $H_2PO_4^-$, $PO_4^-$, lysinate, $HCO_3^-$, a carboxylic acid anion, a dicarboxylic acid anion, and $Cl^-$;
(ii) maintaining the mixture under pre-treatment conditions sufficient to dissolve at least a portion of the polysaccharide present in the biomass, wherein the pre-treatment conditions comprise a temperature of at least about 20° C. and less than about 100° C. for a duration of at least about 0.5 hours.

Biomass

The methods of the invention are used for the pre-treatment of biomass (containing polysaccharide and lignin). The pre-treated biomass can be hydrolyzed to a sugar composition in a saccharification step. The sugar composition can be used as chemical or fermentation feedstocks. The feedstocks, in turn, can be used for the production of ethanol, plastics, or other products or intermediates. Biomass can include, but is not limited to, wood resources, municipal solid waste, wastepaper, and crop residues (see, for example, Wiselogel et al., 1995, in Handbook on Bioethanol (Charles E. Wyman, editor), pp. 105-118, Taylor & Francis, Washington D.C.; Wyman, 1994, Bioresource Technology 50: 3-16; Lynd, 1990, Applied Biochemistry and Biotechnology 24/25: 695-719; Mosier et al., 1999, Recent Progress in Bioconversion of Lignocellulosics, in Advances in Biochemical Engineering/Biotechnology, T. Scheper, managing editor, Volume 65, pp. 23-40, Springer-Verlag, New York). Other examples of biomass include, without limitation, crops such as starch crops (e.g., corn, wheat, or barley), sugar crops (e.g., sugarcane, energy cane or sugar beet), forage crops (e.g., grasses, alfalfa, or clover), and oilseed crops (e.g., soybean, sunflower, or safflower); wood products such as trees, shrubs, and wood residues (e.g., sawdust, bark or the like from forest clearings and mills); waste products such as municipal solid waste (MSW; e.g., paper, food and yard wastes, or wood), process waste, and paper sludge; and aquatic plants such as algae, water weeds, water hyacinths, or reeds and rushes. Other examples of biomass include sorghum, rice hulls, rice straw, wheat straw, and other straws.

Biomass materials typically contain a mixture of polysaccharide species. In many instances, the predominant polysaccharide in the biomass is cellulose, the second most abundant is hemi-cellulose, and the third is pectin. The biomass can also contain polymeric lignin covalently cross-linked to hemicellulose.

Cellulose is a homopolymer of anhydrocellobiose and thus a linear β-(1-4)-D-glucan, while hemicelluloses include a variety of sugar subunits, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

In addition to the polysaccharides described above, biomass typically contains lignin. Lignin is a phenylpropane polymer of monolignol monomers. It is generally found as an integral part of the secondary cell walls of plants and certain types of algae. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Gymnosperms have a lignin that consists almost entirely of G with small quantities of H. That of dicotyledonous angiosperms is more often than not a mixture of G and S (with very little H), and monocotyledonous lignin is a mixture of all three. Many grasses have mostly G, while some palms have mainly S. All lignins contain small amounts of incomplete or modified monolignols, and other monomers are prominent in non-woody plants. Unlike cellulose and hemicellulose, lignin cannot be depolymerized by hydrolysis. Cleavage of the principal bonds in the lignin polymer generally proceeds through oxidation.

In some embodiments, the biomass is derived from corn stover, corn fiber, hard wood, softwood, cereal straw, switchgrass, *Miscanthus*, rice hulls, municipal solid waste (MSW), industrial organic waste, office paper, or mixtures thereof. In some embodiments, the biomass is mechanically separated or reduced in size prior to combining into the pre-treatment mixture or during pre-treatment. Methods for mechanically separating or reducing in size include, but are not limited to, chipping, milling, powdering, pulverizing, or crushing. Thus, the biomass introduced into the pre-treatment mixture before pre-treatment can be in the form of chips (e.g., wood chips), powder, saw dust, flakes, and the like.

Ionic Liquids

A number of ionic liquids can be used in the methods of the invention. In general, the ionic liquid or mixture thereof is suitable for pretreatment of the biomass. In some cases, the ionic liquid or mixture thereof is compatible with glycoside hydrolases used for saccharification of cellulose and other polysaccharides. In some cases, the ionic liquid or mixture thereof is suitable for pre-treatment at a high concentration and/or pH, and compatible with glycoside hydrolases at a reduced concentration and/or pH.

The ionic liquids used in the methods of the invention can contain any suitable cation. Suitable cations include, but are not limited to, ammonium cations.

Examples of ammonium cations include, but are not limited to, 2-hydroxyethyl-trimethylammonium, benzyldimethyltetradecylammonium, benzyltrimethylammonium, butyltrimethylammonium, choline, diethylmethyl(2-methoxyethyl)ammonium, ethyldimethylpropylammonium, methyltrioctadecylammonium, methyltrioctylammonium, tetrabutylammonium, tetradodecylammonium, tetraethylammonium, tetraheptylammonium, tetrahexadecylammonium, tetrahexylammonium, tetrakis(decyl)ammonium, tetramethylammonium, tetraoctylammonium, tributylmethylammonium, triethylmethylammonium, and tris(2-hydroxyethyl)methylammonium.

The cation be, for example, $(C_{1-3}\ \text{alkyl})_x(C_{6-12}\ \text{alkyl})_y N^+$ or $(C_{1-2}\ \text{alkyl})_x(C_{6-8}\ \text{alkyl})_y N^+$, wherein subscript x and subscript y are each 0, 1, 2, 3, or 4, and the sum of x and y is 4. Alternatively, the cation can be, for example, $(C_{1-6}\ \text{alkyl})N^+$.

In some embodiments, a mixture containing the ionic liquid (e.g., a pre-treatment mixture) contains a mixture of ionic liquids. For example, the mixture can contain two different ionic liquids, each ionic liquid having a cation selected from $(C_{1-6}\ \text{alkyl})N^+$ and an anion selected from $OH^-$, $HSO_4^-$, $H_2PO_4^-$, $PO_4^-$, lysinate, $HCO_3^-$, and $Cl^-$. In some cases the cation in the different ionic liquids in the mixture are the same and the anion is different. In some cases the cation in the different ionic liquids in the mixture are different and the anion is the same or different. In some cases, the anion in the different ionic liquids in the mixture are the same and the cation is different. In some cases the mixture contains 2, 3, 4, 5, 6, 7, or 8, or more different ionic liquids.

As described in more detail below, the pH of mixture containing the ionic liquid solution can be reduced after the pretreatment step so that mixture is compatible with enzymes, such as cellulases, used to break down the pre-treated biomass. In certain embodiments, the pH is reduced by adding an acid corresponding to an anion that is present in the ionic liquid. For example, if the anion is a $HSO_4^-$ anion, then $H_2SO_4$ may be added. Alternatively, in some embodiments, the pH is reduced by adding a different acid. In some embodiments, $CO_2$ is added to reduce the pH.

The ionic liquid solution can contain any suitable amount of water. In general, the ionic liquid solutions used in the methods of the invention contain from about 0.1% water to about 95% water by weight of the ionic liquid solution. An ionic liquid solution can contain, for example, from about 5% to about 90% water, or from about 10% to about 80% water, or from about 20% to about 60% water, or from about 30% to about 50% water, or from about 0.1% to about 50% water, or from about 5% to about 45% water, or from about 10% to about 40% water, or from about 15% to about 35% water, or from about 20% to about 30% water by weight of the ionic liquid solution. An ionic liquid solution can contain, for example, from about 20% to about 60% water, or from about 25% to about 55% water, or from about 30% to about 50% water, or from about 30% to about 60% water, or from about 35% to about 55% water, or from about 40% to about 50% water, or from about 10% to about 35% water, or from about 25% to about 45% water by weight of the ionic liquid solution. The ionic liquid solution can contain about 0.1, 1, 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, or about 95% water by weight of the ionic liquid solution.

In certain embodiments, the ionic liquid solution contains from about 70% (w/w) to about 95% (w/w) water. The ionic liquid solution can contain from about 70% to about 75% water, or from about 75% to about 80% water, or from about 80% to about 85% water, or from about 85% to about 90% water, or from about 90% to about 95% water by weight of the ionic liquid solution. The ionic liquid solution can contain from about 70% to about 90% water, or from about 72% to about 85% water, or from about 73% to about 80% water by weight of the ionic liquid solution. The ionic liquid solution can contain from about 70% to about 95% water, or from about 80% to about 93% water, or from about 85% to about 92% water by weight of the ionic liquid solution.

In some embodiments, the ionic liquid solution can contain from about 10% (w/w) to about 95% (w/w) ionic liquid. The ionic liquid solution can contain from about 20% to about 90% ionic liquid, or from about 25% to about 80% ionic liquid, or from about 25% to about 70% ionic liquid, or from about 25% to about 60% ionic liquid, or from about 25% to about 55% ionic liquid by weight of the ionic liquid solution. The ionic liquid solution can contain from about 30% to about 70% ionic liquid, or from about 30% to about 60% ionic liquid, or from about 30% to about 50% ionic liquid by weight of the ionic liquid solution. The ionic liquid solution can contain from about 35% to about 65% ionic liquid, or from about 35% to about 60% ionic liquid, or from about 35% to about 55% ionic liquid, or about 25%, 30%, 35%, 40%, 45%, or 50% ionic liquid by weight of the ionic liquid solution.

Other amounts of water and ionic liquid can be used in the methods of the invention, depending in part on factors such as the type of biomass material to be treated and the particular cations and anions to be included in the ionic liquid.

Biomass Pretreatment

Pretreatment of the biomass in the solution containing the ionic liquid or mixture of ionic liquids can be conducted for a suitable length of time at a suitable temperature and pressure. In general, pretreatment is conducted for anywhere from a few minutes to several hours. Pretreatment can be conducted, for example, for about five minutes, or about 10 minutes, or about 30 minutes, or about 60 minutes. Pretreatment can be conducted for about 0.5, 1, 1.5, 2, 2.5, 3, 3.5, 4, 4.5, 5, 5.5, 6, 9, 12, 15, 18, 21, 24, 36, 48, 60, or about 72 hours. Pretreatment is generally conducted at a temperature ranging from about 10° C. to about 200° C.

The pretreatment mixture can contain a suitable amount of biomass. In general, the pretreatment mixture contains up to about 50% biomass by weight of the pretreatment mixture. The pretreatment mixture can contain, for example, from about 0.1 to about 50% biomass, or from about 5% to about 45% biomass, or from about 10% to about 40% biomass, or from about 15% to about 35% biomass, or from about 20% to about 30% biomass, or from about 5% to about 40% biomass, or from about 5% to about 30% biomass, or from about 5% to about 20% biomass, or from about 5% to about 100% biomass by weight of the pretreatment mixture. The pretreatment mixture can contain about 1, 5, 10, 15, 20, 25, 30, 35, 40, 45, or 50% biomass by weight of the pretreatment mixture. In some embodiments, the mixture includes from about 5% (w/w) to about 30% (w/w) biomass. Other amounts of biomass can be used in the methods of the invention, depending in part on factors such as the type of biomass material and the particular ionic liquid used in the method.

The pre-treatment mixture can contain a suitable amount of water and ionic liquid. In general, the pre-treatment mixture contain from about 0% water (i.e., using a neat ionic liquid solution for pre-treatment) to about 95% water by weight of the ionic liquid in the pre-treatment mixture or by weight of the pre-treatment mixture. A pre-treatment mixture can contain, for example, from about 5% to about 90% water, or from about 10% to about 80% water, or from about 20% to about 60% water, or from about 30% to about 50% water, or from about 0.1% to about 50% water, or from about 5% to about 45% water, or from about 10% to about 40% water, or from about 15% to about 35% water, or from about 20% to about 30% water by weight of the ionic liquid in the pre-treatment mixture or by weight of the pre-treatment mixture. A pre-treatment mixture can contain, for example, from about 20% to about 60% water, or from about 25% to about 55% water, or from about 30% to about 50% water, or from about 30% to about 60% water, or from about 35% to about 55% water, or from about 40% to about 50% water, or from about 10% to about 35% water, or from about 25% to about 45% water by weight of the ionic liquid in the pre-treatment mixture or by weight of the pre-treatment mixture. The pre-treatment mixture can contain about 0.1, 1, 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, or about 95% water by weight of the ionic liquid in the pre-treatment mixture or by weight of the pre-treatment mixture.

In certain embodiments, the pre-treatment mixture contains from about 70% (w/w) to about 95% (w/w) water. The pre-treatment mixture can contain from about 70% to about 75% water, or from about 75% to about 80% water, or from about 80% to about 85% water, or from about 85% to about 90% water, or from about 90% to about 95% water by weight of the pre-treatment mixture. The pre-treatment mixture can contain from about 70% to about 90% water, or from about 72% to about 85% water, or from about 73% to about 80% water by weight of the pre-treatment mixture. The ionic liquid solution can contain from about 70% to about 95% water, or from about 80% to about 93% water, or from about 85% to about 92% water pre-treatment mixture.

In certain embodiments, the pre-treatment mixture contains from about 0% (w/w) to about 45% (w/w) water, from about 0% to about 40% (w/w) water, from about 0% to about 35% (w/w) water, from about 0% to about 30% (w/w) water, from about 0% to about 25% (w/w) water, from about 0% to about 20% (w/w) water, from about 0% to about 15% (w/w) water, or from about 0% to about 10% (w/w) water. In certain embodiments, the pre-treatment mixture contains from about 5% (w/w) to about 45% (w/w) water, from about 5% to about 40% (w/w) water, from about 5% to about 35% (w/w) water, from about 5% to about 30% (w/w) water, from about 5% to about 25% (w/w) water, from about 5% to about 20% (w/w) water, from about 5% to about 15% (w/w) water, or from about 5% to about 10% (w/w) water. The pre-treatment mixture can contain from about 5% to about 40% water, or from about 75% to about 80% water, or from about 80% to about 85% water, or from about 85% to about 90% water, or from about 90% to about 95% water by weight of the pre-treatment mixture. The pre-treatment mixture can contain from about 70% to about 90% water, or from about 72% to about 85% water, or from about 73% to about 80% water by weight of the pre-treatment mixture. The ionic liquid solution can contain from about 70% to about 95% water, or from about 80% to about 93% water, or from about 85% to about 92% water pre-treatment mixture.

In some embodiments, the pre-treatment mixture can contain from about 10% (w/w) to about 95% (w/w) ionic liquid. The pre-treatment mixture can contain from about 20% to about 90% ionic liquid, or from about 25% to about 80% ionic liquid, or from about 25% to about 70% ionic liquid, or from about 25% to about 60% ionic liquid, or from about 25% to about 55% ionic liquid by weight of the pre-treatment mixture. The pre-treatment mixture can contain from about 30% to about 70% ionic liquid, or from about 30% to about 60% ionic liquid, or from about 30% to about 50% ionic liquid by weight of the pre-treatment mixture. The pre-treatment mixture can contain from about 35% to about 65% ionic liquid, or from about 35% to about 60% ionic liquid, or from about 35% to about 55% ionic liquid, or about 25%, 30%, 35%, 40%, 45%, or 50% ionic liquid by weight of the pre-treatment mixture. The pre-treatment mixture can contain from about 30% to about 90% ionic liquid, or from about 35% to about 85% ionic liquid, or from about 40% to about 80% ionic liquid, or from about 45% to about 75% ionic liquid, or from about 55% to about 70% ionic liquid, or from about 60% to about 65% ionic liquid by weight of the pre-treatment mixture.

Generally, the methods described herein are suitable for pre-treatment at lower temperatures. Thus, in some embodiments, pre-treatment can be conducted at a temperature ranging from about 10° C. to about 130° C., or 20° C. to about 130° C. In some embodiments, the methods described herein provide improved pre-treatment at temperatures at or above room temperature. Thus, in some embodiments, pre-treatment can be conducted at a temperature ranging from about 25° C. to about 130° C. Pretreatment can be conducted, for example, at a temperature ranging from about 20° C. to about 100° C., or from about 25° C. to about 100° C., or from about 30° C. to about 80° C., or from about 35° C. to about 70° C., or from about 35° C. to about 65° C., or from about 35° C. to about 60° C., or from about 35° C. to about 55° C., or from about 40° C. to about 55° C., or from about 45° C. to about 55° C., or from about 30 to about 130° C., or from about 35 to about 130° C., or from about 40 to about 130° C., or from about 45 to about 130° C., or from about 50 to about 130° C., or from about 30 to about 100° C., or from about 35 to about 100° C., or from about 40 to about 100° C., or from about 45 to about 100° C., or from about 50 to about 100° C.

The lower temperature pre-treatment conditions described herein can reduce the steam requirement for biomass pre-treatment. In some cases, the pre-treatment conditions can be maintained with less than about 100 MT/hr, 95 MT/hr, 90 MT/hr, 85 MT/hr, 80 MT/hr, 75 MT/hr, 70 MT/hr, 65 MT/hr, 60 MT/hr, 55 MT/hr, 50 MT/hr, 45 MT/hr, 40 MT/hr, 35 MT/hr, 30 MT/hr, or 25 MT/hr of steam to process about 2000 MT/day of dry biomass. In some cases, the pre-treatment conditions can be maintained with from about 25 MT/hr to about 100 MT/hr, about 35 MT/hr to about 95

MT/hr, about 40 MT/hr to about 90 MT/hr, or about 50 MT/hr to about 85 MT/hr of steam to process about 2000 MT/day of dry biomass.

In some cases, the pre-treatment conditions can be maintained with from about 25 MT/hr to about 80 MT/hr, about 35 MT/hr to about 75 MT/hr, about 40 MT/hr to about 70 MT/hr, or about 50 MT/hr to about 65 MT/hr of steam to process about 2000 MT/day of dry biomass. In some cases, the pre-treatment conditions can be maintained with from about 25 MT/hr to about 70 MT/hr, about 35 MT/hr to about 65 MT/hr, or about 40 MT/hr to about 60 MT/hr, of steam to process about 2000 MT/day of dry biomass. In some cases, the pre-treatment conditions can be maintained with from about 25 MT/hr to about 60 MT/hr, about 35 MT/hr to about 55 MT/hr, or about 40 MT/hr to about 50 MT/hr of steam to process about 2000 MT/day of dry biomass. In some cases, the pre-treatment conditions can be maintained with from about 5 MT/hr to about 60 MT/hr, about 10 MT/hr to about 55 MT/hr, or about 15 MT/hr to about 50 MT/hr of steam to process about 2000 MT/day of dry biomass. In some cases, the pre-treatment conditions can be maintained with from about 5 MT/hr to about 50 MT/hr, about 10 MT/hr to about 40 MT/hr, about 10 MT/hr to about 35 MT/hr, about 10 MT/hr to about 45 MT/hr, about 15 MT/hr to about 35 MT/hr, or about 15 MT/hr to about 40 MT/hr of steam to process about 2000 MT/day of dry biomass.

Pretreatment can be conducted at about 25, 30, 35, 40, 45, 50, 55, 60, 65, 70, 75, 80, 85, 90, 95, 100, 105, 110, 115, 120, 125, 130, or 135° C. for at least about 0.5, 1, 3, 6, 9, 12, or 16 hours. Pretreatment can be conducted at atmospheric pressure or elevated pressures. Pretreatment can be conducted, for example, at a pressure (Pg) ranging from about 14 psi to about 4000 psi, or from about 14 psi to about 3500 psi, or from about 14 psi to about 2500 psi, or from about 14 psi to about 1500 psi. In certain embodiments, the pretreatment is conducted at around atmospheric pressure (i.e., 14.696 psi).

In general, the pH of the pre-treatment mixture is at or above 7. The pH of the pre-treatment mixture can be, for example, at least 7, at least 7.5, at least 8, at least 8.5, at least 9, at least 9.5, at least 10, at least 10.5, at least 11, at least 11.5, at least 12, at least 12.5, from about 7.5 to about 14, from about 8 to about 13, or from about 9 to about 12. One of skill in the art will appreciate that the pH of the pre-treatment mixture will vary depending on the particular anion and cation used, the ratio of the anion and the cation, and their absolute concentrations.

Typical embodiments described herein provide conditions sufficient to remove a significant fraction of lignin in the biomass. Removal of lignin can increase the efficiency of one or more downstream steps, such as saccharification, fermentation, or other pre-treatment steps, or a combination thereof. In some cases, the pre-treatment conditions described herein can remove at least 25%, 30%, 35%, 40%, 45%, 50%, 55%, 60%, 65%, 70%, 75%, 80%, 85%, 90%, or more of the lignin in the biomass prior to pre-treatment. In some cases, the pre-treatment conditions described herein can remove from about 25% to about 95%, from about 30% to about 90%, from about 35% to about 85%, from about 40% to about 80%, from about 45% to about 75%, from about 50% to about 70%, or from about 55% to about 65% of the lignin in the biomass prior to pre-treatment. In some cases, the pre-treatment conditions described herein can remove from about 45% to about 95%, from about 50% to about 90%, from about 55% to about 85%, from about 60% to about 80%, or from about 65% to about 75% of the lignin in the biomass prior to pre-treatment. In some cases, the pre-treatment conditions described herein can remove from about 45% to about 85%, from about 50% to about 80%, from about 55% to about 75%, or from about 60% to about 70 of the lignin in the biomass prior to pre-treatment.

Biomass Saccharification

In some embodiments, the method includes:
(i) providing a pre-treatment mixture comprising biomass at a concentration of at least about 5% (w/w), an ionic liquid or mixture of ionic liquids at a concentration of at least about 40% w/w, and optionally water, wherein the biomass comprises lignin and polysaccharide, and wherein the ionic liquid or mixture thereof comprises:
   a) a tetrabutylammonium cation; and
   b) an anion, such as an hydroxide anion (OH—), a bicarbonate anion ($HCO_3^-$), a carboxylic acid anion, a dicarboxylic acid anion, and a chloride anion ($Cl^-$);
(ii) maintaining the mixture under pre-treatment conditions sufficient to dissolve at least a portion of the polysaccharide present in the biomass, wherein the pre-treatment conditions comprise a temperature of at least about 15° C. and less than about 65° C. for a duration of at least about 0.5 hours;
(iii) optionally diluting the pre-treatment mixture with a polar solvent to form a diluted pre-treatment mixture, and optionally collecting pre-treated biomass solids from the diluted pre-treatment mixture; and
(iv) contacting the pre-treated biomass solids with a glycoside hydrolase under conditions sufficient to hydrolyze at least a portion of the polysaccharide, thereby forming a sugar composition, wherein the sugar composition comprises at least one monosaccharide or oligosaccharide.

In some embodiments, the dilution step is not required. Rather, the pH of the pre-treatment mixture is adjusted to be compatible with one or more glycoside hydrolases, and the pre-treated biomass (e.g., the pH adjusted pre-treatment mixture) is contacted with a glycoside hydrolase under conditions sufficient to hydrolyze at least a portion of the polysaccharide, thereby forming a sugar composition, wherein the sugar composition comprises at least one monosaccharide or oligosaccharide. In some cases, the pre-treatment mixture is diluted with a polar solvent (e.g., water) and the pH is adjusted to be compatible with one or more glycoside hydrolases, and the pre-treated biomass (e.g., the pH adjusted pre-treatment mixture) is contacted with a glycoside hydrolase under conditions sufficient to hydrolyze at least a portion of the polysaccharide, thereby forming a sugar composition, wherein the sugar composition comprises at least one monosaccharide or oligosaccharide.

Thus, in some embodiments, following pre-treatment of the biomass, the pH of the pre-treatment mixture (e.g., diluted with a polar solvent after pretreatment, or undiluted) or a slurry containing the biomass solids collected from the pre-treatment mixture is reduced to a level that is suitable for enzymatic hydrolysis of the polysaccharide by one or more glycoside hydrolases. In general, the pH of mixture is reduced to at most about 7. The pH of the mixture can be reduced, for example, to less than 7, at or about 6.5, at or about 6, at or about 5.5, at or about 5, at or about 4.5, or at or about 4.0. In certain embodiments, the pH of the pre-treatment mixture is reduced to a pH of from about 4 to about 6, or from about 4.5 to about 6.5, or from about 4.8 to about 6.2, or from about 4.8 to about 5.2, or from about 5.2 to about 6.5, or from about 5.2 to about 6.2. The pH of the pre-treatment mixture can be reduced by adding an acid to the mixture. Any suitable acid can be used to reduce the pH. Suitable acids include, but are not limited to, hydrochloric acid, sulfuric acid, nitric acid, acetic acid, citric acid, formic acid, and the like. One of skill in the art will appreciate that the pH of the pre-treatment mixture can be adjusted to maximize the activity of an enzyme, or a mixture of enzymes, e.g., one or more glycoside hydrolases, used in the subsequent hydrolysis step. The particular pH will depend in part on factors including, but not limited to, the specific glycoside hydrolase(s) and the amount of ionic liquid in the mixture.

In some embodiments, dilution of the pre-treatment mixture is performed with a polar solvent selected from the group consisting of water, methanol, ethanol, propanol, isopropanol, butanol, pentanol, hexanol, heptanol, octonol, or isooctonol. In some cases, the polar solvent is water. In some embodiments, the method comprises diluting the pre-treatment mixture with from about 2 volumes of polar solvent to about 10 volumes of polar solvent.

Accordingly, some embodiments of the invention provide a method for preparing a sugar composition as described above wherein step iii) includes adding an acid to the mixture resulting from step ii). In some such embodiments, the acid used in step iii) is the same as a dicarboxylic acid used in step i). In some such embodiments, the molar amount of acid in step iii) is equal to the molar amount of acid in step i).

The methods of the invention generally include adding on or more enzymes that break down polysaccharide biomass into smaller components. Typically, the pretreated biomass is subjected to the action of one, or multiple, enzyme activities selected from a protease, a lipase, a cellulase, an amylase, a glucano-hydrolase, a pectinase, a xylanase, a ferulic acid esterase, and a mannanase. The pretreated biomass may also be treated with other enzymes, e.g., hemicellulases, that are used for the degradation of biomass.

In some embodiments, the glycoside hydrolase is selected from an endoglucanase, an exoglucanase, a β-glucosidase, a xylanase, and mixtures thereof. In some embodiments, one or more cellulases are added to the pretreated biomass present in the ionic liquid mixture in which the pH has been reduced, e.g., to at least about 7, following treatment at a high pH.

A "cellulase" as used herein is a glycoside hydrolase enzyme that hydrolyzes cellulose (β-1,4-glucan or β-D-glucosidic linkages) resulting in the formation of glucose, cellobiose, cellooligosaccharides, and the like. In the context of the present invention, cellulases include endoglucanases; exoglucanases or cellobiohydrolases; and β-glucosidases. Endoglucanases (EC 3.2.1.4) including endo-1,4-β-glucanases or 1,4-β-D-glucan-4-glucanohydrolases, act randomly on soluble and insoluble 1,4-β-glucan substrates. Exoglucanases (exo-1,4-β-D-glucanases, e.g., the 1,4-β-D-glucan glucohydrolases; EC 3.2.1.74) liberate D-glucose from 1,4-β-D-glucans and hydrolyze D-cellobiose slowly. Cellobiohydrolases (1,4-β-D-glucan cellobiohydrolases, EC 3.2.1.91) liberate D-cellobiose from 1,4-β-glucans. β-Glucosidases ([β]-D-glucoside glucohydrolase; β-D-glucosidases; EC 3.2.1.21) act to release D-glucose units from cellobiose and soluble cellodextrins, as well as an array of glycosides. Endoglucanases act mainly on the amorphous parts of the cellulose fiber, whereas cellobiohydrolases are also able to degrade crystalline cellulose.

A combination of two or more cellulases can be used in the methods of the invention. Cellulases act in concert to catalyze the hydrolysis of cellulose-containing substrates. For example, endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. β-glucosidases split the cellobiose into glucose monomers. The cellulase can be a thermostable cellulase. In certain embodiments the glycoside hydrolase, such as a cellulase, is selected such that it can perform optimally in the presence of ionic liquid.

A xylanase and/or a "mannanase" may also be employed in the saccharification of pretreated biomass. A "xylanase" is a glycoside hydrolase enzyme that catalyzes the endo-hydrolysis of 1,4-β-D-xylosidic linkages in xylans. Xylanases include enzymes classified as a 1,4-β-D-xylan-xylohydrolase (E.C. 3.2.1.8).

A "mannanase" is a glycoside hydrolase that hydrolyzes 1,4-β-D-mannosidic linkages in mannans, galactomannans and/or glucomannans. "Mannanase activity" refers to hydrolysis of 1,4-β-D-mannosidic linkages in mannans, galactomannans and/or glucomannans. Mannases include enzymes classified as EC 3.2.1.78.

Cellulases suitable for use in the present invention are commercially available from, for example, Genencor (USA) and Novozymes (Europe). For instance, Novozyme has a number of different enzymes and enzyme complexes that are specifically designed to be useful for the hydrolysis of lignocellulosic materials. Examples include, but are not limited to, the following: NS50013, which is a cellulase; NS50010, which is a β-glucosidase; NS22086, which is a cellulase complex; NS22086, which is a xylanase; NS22118, which is β-glucosidase; NS22119, which is an enzyme complex of carbohydrases, including arabinase, β-glucanase, cellulase, hemicellulase, pectinase, and xylanase; NS22002, which is a mixture of β-glucanase and xylanase; and NS22035, which is a glucoamylase. In addition, suitable thermostable cellulases are disclosed in PCT International Publication No. WO 2010/124266, the teachings of which are incorporated herein by reference. Other hydrolases suitable for hydrolyzing the pretreated biomass, i.e., the lignocellulosic material, will be known to those of skill in the art. See e.g., Viikari et al., *Adv. Biochem. Eng. Biotechnol.*, 108:121-45, 2007; and U.S. Patent Application Nos. 2009/0061484; US 2008/0057541, and US 2009/0209009, which are incorporated by reference.

Any suitable amount of enzyme or enzyme mixture, e.g., glycoside hydrolase or mixture of glycoside hydrolases, can be used in the methods of the invention. In general a sub-stoichiometric amount of the glycoside hydrolase, with respect to the polysaccharide present in the pre-treated biomass, is used. The amount of glycoside hydrolase can be expressed as activity units. Alternatively, the amount of the glycoside hydrolase used in the methods of the invention can be expressed relative to the amount of biomass treated in the pretreatment step. For example, the hydrolysis mixture can contain a glycoside hydrolase (or a mixture of glycoside hydrolases) in an amount ranging from about 0.01 to about 10% (w/w), with respect to the amount of biomass used in the pretreatment step. Thus, for example, when the method is conducted using 1 kg of biomass, for example, the hydrolysis step can be conducted with a glycoside hydrolase or a mixture of glycoside hydrolases in an amount ranging from about 100 mg to about 100 g. Those of skill in the art will appreciate that the amount of glycoside hydrolase or mixture of enzymes used in the methods of the invention will depend in part on factors including, but not limited to, the particular enzyme used, the nature of the biomass source, and the extent of the pretreatment step.

The enzymatic hydrolysis step can be conducted for any length of time at any suitable temperature. The enzymatic hydrolysis step can be conducted, for example, for about 2, 5, 10, 15, 30, 45, or 60 minutes. The enzymatic hydrolysis step can be conducted for about 1, 1.5, 2, 2.5, 3, 3.5, 4, 4.5, 5, 5.5, 6, 9, 12, 15, 18, 21, 24, 30, 36, 42, 48, or 72 hours. Enzymatic hydrolysis is generally conducted at a temperature ranging from about 20° C. to about 60° C. Enzymatic hydrolysis can be conducted, for example, at a temperature ranging from about 20° C. to about 40° C., or from about 40° C. to about 60° C. Enzymatic hydrolysis can be conducted at about 25° C., about 37° C., or about 55° C. for at least about 10, 20, 30, 60, or 90 minutes or for at least about 2, 3, 4, 5, 6, 7, 8, 9, 10, 11, 12, 24, 48, or 72 hours.

Sugar Compositions

The methods of the invention provide sugar compositions containing one or monosaccharides and/or oligosaccharides. Monosaccharides present in the sugar compositions can include, but are not limited to, fucose, arabinose, rhamnose, galactose, mannose, xylose, glucose, glucuronic acid, and galacturonic acid. The oligosaccharides in the sugar compositions contain monosaccharide subunits (e.g., fucose, arabinose, rhamnose, galactose, mannose, xylose, glucose, glucuronic acid, and galacturonic acid) linked together via glycosidic bonds. Typically, between about 10% and about 100% conversion of the polysaccharide biomass to sugars results from the methods of the invention. Thus, e.g., processing of 1 kg of polysaccharide biomass according to the methods of the invention can yield from about from about 110 g to about 1100 g of the constituent monosaccharides and oligosaccharides in the final sugar compositions. For example, processing of 1 kg of switchgrass according to the methods of the invention can yield sugar compositions containing from about 0.1 g to about 350 g of glucose and from about 0.1 g to about 210 g to xylose. One of skill in the art will appreciate that the components and the yield of the sugar composition will depend, in part, on the specific source of the biomass and the specific conditions that are used for pretreatment and hydrolysis.

Fermentation

The sugar compositions produced via the methods of the invention can, in turn, be used as carbon sources for host cells to produce useful organic compounds such as biofuels. Examples of such products include, but are not limited to, alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, β-carotene); fatty acids and fatty acid derivatives (as described, e.g., in PCT/US2008/068833); isoprenyl alkanoates (as described, e.g., PCT/US2008/068756, methyl butenol (as described, e.g., PCT/US2008/068831; fatty acid esters (as described, e.g., in PCT/US2010/033299), isoprenoid-based alternative diesel fuel (as described, e.g., in PCT/US2011/059784; a polyketide synthesized by a polyketide synthase, such as a diacid (see, e.g., PCT/US2011/061900), biofuels (see, e.g., PCT/US2009/042132) and alpha-olefins (see, e.g., PCT/US2011/053787).

Accordingly, some embodiments of the invention provide a method for converting a sugar composition to a fermentation product, wherein the method includes fermenting a mixture containing a sugar composition prepared according to the methods described above.

In certain embodiments, fermenting the sugar composition is conducted without removing the ionic liquid. That is, the fermentation step is conducted in the mixture containing the ionic liquid and the fermentable sugars resulting from step v) of the method described above (i.e., a crude sugar composition). In such embodiments, fermenting the sugar composition comprises adding a fermentation microorganism to the mixture containing the sugar composition and the ionic liquid. The mixture containing the sugar composition and the ionic liquid can be diluted (e.g., with growth medium such as EZ-dex growth medium, a buffer, or combinations thereof) prior to addition of the microorganisms so as to maintain the viability of the microorganisms during the fermentation process. In some embodiments, the mixture is diluted such that the concentration of the ionic liquid is less than about 15% (w/w). For example, the mixture can be diluted such that the concentration of the ionic liquid is less than about 15, 14, 13, 12, 11, 10, 9, 8, 7, 6, 5, 4, 3, 2, or 1% (w/w). The mixture containing the sugar composition and the ionic liquid can be supplemented by addition of additional sugars such as additional glucose or additional xylose.

Organisms employed for fermentation may be wild-type organisms or may be genetically modified. Such organisms are well known and include bacteria, yeast, microalgae, and filamentous fungi. In some embodiments, the yeast is a *Saccharomyces* sp. e.g., *Saccharomyces cerevisiae* or *Saccharomyces uvarum*. Other yeast may also be employed, e.g., *Kluyveromyces*, such as *Kluyveromyces marxianus*, *Kluyveromyces lactis* or *Kluyveromyces fragilis; Candida*, such as *Candida pseudotropicalis* or *Candida brassicae*; a *Hansenula, Pichia*, such as *Pichia pastoris, Saccharomyces, Schizosaccharomyces*, such as *Schizosaccharomyces porn be*, or *Yarrowia* sp. Examples of fermenting bacteria that may be used include *E. coli, Klebsiellan* sp., *Bacillus* sp., *Clostridium* sp., *Zymomonas* sp. and others (for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis*). Examples of filamentus fungi include *Aspergillus* sp., *Trichoderma* sp., *Myceliopthera* sp., and *Neurospora* sp.

Examples of products that can be obtained from microorganisms in the fermentation step of the method include, but are not limited to: ethanol obtained from *Saccharomyces, Schizosaccharomyces, Saccharomycodes, Torulopsis, Kluyveromyces, Zymomonas mobilis*, or *E. coli*; tartaric acid obtained from Lactobacilli; itaconic acid obtained from *Aspergillus terreus* or *Aspergillus itaconicus*; succinic acid obtained from *Actinobacillus* sp. 130Z, *Anaerobiospirillum succiniproducens, Actinobacillus succinogenes*, or *E. coli*; hydroxypropionic acid obtained from *Lactobacillus delbrückii, L. leichmannii*, or *Sporolactobacillus inulinus*; propionic acid obtained from *Propionibacterium* or *Clostridium propionicum*; citric acid obtained from an *Aspergillus* sp., such as *Aspergillus niger* or *Aspergillus wentii*; aconitic acid obtained from *Aspergillus niger* or *Aspergillus wentii*; malic acid obtained from *Aspergilli, A. niger. A. oryzae*, or *Corynebacterium*; gluconic acid obtained from *Aspergilli*; butyric acid obtained from *Clostridium*; lactic acid obtained from *Lactobacillus*; eicosapentaenic acid obtained from *Mortiella, Phytium, Rhodopseudomonas*, or *Shewanella* spp.; propanediol obtained from *E. coli*; butanediol obtained from *Enterobacter aerogenes, Bacillus subtilis*, or *Klebsiella oxytoca*; butanol obtained from *Clostridium* spp.; glycerol obtained from *Saccharomyces rouxii*; mannitol obtained from *Aspergillus candida* or *Torulopsis mannitofaciens*; acetone obtained from *Clostridium*; and gibberellic acid obtained from *Gibberella fujikuroi*.

In some embodiments, *E. coli* or a yeast, such as *Saccharomyces cerevisiae* is used for fermenting the sugar composition in a fermentation conducted without removing the ionic liquid. In some embodiments, fermenting the sugar composition includes producing isopentenol or a bisabolene. In some embodiments, the bisabolene is (E)-1-methyl-4-(6-methylhepta-2,5-dien-2-yl)cyclohex-1-ene; (S)-1-methyl-4-(6-methylhepta-1,5-dien-2-yl)cyclohex-1-ene; (Z)-1-methyl-4-(6-methylhept-5-en-2-ylidene)cyclohex-1-ene; or a mixture thereof.

In certain embodiments, the fermentation step includes extractive fermentation, wherein an extraction solvent is introduced directly into the fermentation mixture so as to remove the product from the fermentation medium as the product is being formed. Any suitable extraction solvent can be used in the methods of the invention. Suitable extraction solvents include, but are not limited to, oleyl alcohol, n-dodecanol, isoamyl acetate, isooctyl alcohol, nonanoic acid, n-butyl acetate, dibutyl ether, and dibutyl oxalate. The properties of the extraction solvent can be chosen so that the extraction solvent separates easily from the fermentation medium for removal from an apparatus such as a fermenter. The extraction solvent can also be replenished, so that the extraction process may be carried out continuously. The extractant containing the product can be removed from the fermenter and treated to separate the product from the extractant. The extractant can then be recycled to the fermenter for the extraction of further product.

As a non-limiting example, the process can be carried out in a continuous stirred tank fermenter in which the microorganism cells are freely suspended. In such an apparatus, for steady state operation, the input rate of fresh substrate solution (known as the dilution rate, i.e., the input flow rate divided by the volume of the fermenter) can be set such that the rate of cell removal in the outflowing medium is equal to the rate of cell production in the fermenter. In this way, the microorganism cell population remains substantially constant.

The extraction solvents disclosed herein may also be used with batchwise fermentation, or fed-batch fermentation or immobilized cell fermentation. Alternatively, downstream extraction can be conducted in a separate step. In such a process, the liquid-liquid extraction of the product is carried out on fermentation medium removed from the fermenter. After separation of the fermentation medium from the extractant/product solution, the medium may be recycled to the fermenter, discarded or treated for the removal of any remaining product.

During the extraction step, the extractant is preferably brought into intimate contact with the aqueous medium in order to promote rapid and complete partition of the product. For example, in the case of in situ extraction, the extractant may be introduced in small streams at the bottom of the fermenter and allowed to rise to the surface to form a continuous surface layer.

After separation of the extractant/product solution from the fermentation medium, the product can be removed from the extractant by any suitable means and, as mentioned above, the extractant may then be recovered and reused for further product extraction. For example, the extractant/product solution may be distilled in order to separate the product from the extractant. As an alternative to distillation, the product may be separated from the extractant by stripping with air or $CO_2$, followed by product condensation, or by any other suitable method. Other separation techniques including, but not limited to, distillation, azeotropic distillation, membrane separation, and adsorption onto solid adsorbents are known to those of skill in the art and can be used to separate the fermentation medium from the fermentation products [see, for example, Huang et al. 2008. *Separation and Purification Technology* 62: 1-21].

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

EXAMPLES

Certain ionic liquids (ILs) are able to dissolve either lignocellulosic materials or one of its main constituents such as cellulose, hemicellulose, or lignin. [Brandt A et al., *Green Chemistry*. 2013; 15(3): 550-583]. The IL 1-ethyl-3-methylimidazolium acetate ([$C_2C_1$Im][OAc]) based IL pretreatment process typically requires temperatures above 140° C. for 3 hrs reaction time in order to be effective and typically use pure IL as the pretreatment solvent. [Li C, et al., *Bioresource technology*. 2010; 101(13): 4900-4906; Singh S, Simmons B A, Vogel K P, *Biotechnology and Bioengineering*. 2009; 104(1): 68-75; Shi J, et al., *Biofuels*. 2013; 4(1): 63-72; Sun N, et al., *Green Chemistry*. 2014; 16(5): 2546-2557; Singh S, Simmons B A, *Aqueous Pretreatment of Plant Biomass for Biological and Chemical Conversion to Fuels and Chemicals*. John Wiley & Sons, Ltd, 2013, pp 223-238]. There have been recent efforts focused on the discovery and demonstration of ILs for the pretreatment/fractionation of lignocellulosic materials at less severe process conditions. [Fukaya Y, *Green Chemistry*. 2008; 10(1): 44-46; Shi J, et al., *Green Chemistry*. 2014; 16(8): 3830-3840; Parthasarathi R, et al., *The Journal of Physical Chemistry B*. 2015; 119(45): 14339-14349]. [OH] based ILs with [$C_2C_1$IM] were used for biochemical synthesis such as sugars, [Li L et al., *BioResources*. 2011; 6(4): 4494-4504] biodiesel [Zhou S, *Chinese Chemical Letters*. 2012; 23(4): 379-382] and 5-hydroxymethylfurfural. [Li L et al., *BioResources*. 2011; 6(4): 4494-4504; Qu Y, et al., *Scientific reports*. 2016; 6: 1-7]. Studies on quaternary ammonium cations, such as tetrabutylammonium fluoride trihydrate ([TBA]F), [Heinze T, et al., *Macromolecular Chemistry and Physics*. 2000; 201(6): 627-631] tetraethylammonium chloride ([TEA]Cl), [Changfa X., *Spectroscopy and Spectral Analysis*. 1994; 4] and tetrabutylammonium hydroxides ([TBA][OH]) [Ema T et al., *RSC Advances*. 2014; 4(5): 2523-2525] with co-solvents, were reported to dissolve cellulose rapidly at low temperatures. This rapid dissolution of cellulose at low temperatures has been hypothesized to occur due to the strong proton accepting capacity of the anion, even in the presence of water, that weakens the association of the hydrogen bonding network and destabilizing the cellulose microstructure.

Recent studies using tetrabutylammonium acetate ([TBA][OAc]) with dimethyl sulfoxide (DMSO) and crown ether (18-crown-6) demonstrated the feasibility of 8 wt % cellulose dissolution within 5 min at 40° C. [Miao J et al., *RSC Advances*. 2014; 4(69): 36721-36724]. Tetrabutylphosphonium hydroxides ([TBP][OH]) containing 30-50 wt % water can dissolve cellulose at 25° C., [and Ohno and co-workers recently reported the rapid (~5 min) dissolution of 15 wt % cellulose in aqueous solutions of [TBP][OH] that contained 40-50% water by weight at room temperature. [Abe M, Fukaya Y, Ohno H, *Chemical Communications.* 2012; 48(12): 1808-1810]. Zhong et al. reported cellulose isolation from wheat straw using [TBA][OH] solutions containing 50% water at 60° C. after de-waxed with toluene-ethanol (2:1, v/v) and pretreated in boiling water for 2 hrs. [Zhong C et al, *Carbohydrate Polymers.* 2013; 94(1): 38-45].

Unfortunately, from a biorefinery perspective, all of these methods require multi-step treatments, use of co-solvents, water washes and have not been proven on a wide range of "real world" lignocellulosic biomass substrates such as switchgrass, pine and *eucalyptus*. The possibility of IL pretreatment at lower operating temperatures may facilitate the development of more affordable and practical pretreatment processes with seamless biomass integrated conversion processes. [Tanger P et al., *Frontiers in Plant Science.* 2013; 4(218): 1-20; Tao L, et al., *Bioresource Technology.* 2011; 102(24): 11105-11114] [Klein-Marcuschamer D, Simmons B A, Blanch H W, *Biofuels, Bioproducts and Biorefining.* 2011; 5(5): 562-569].

We report here that the relatively inexpensive [Ferlin N, et al., *Tetrahedron.* 2013; 69(30): 6150-6161] [TBA][OH] processing of lignocellulose can pretreat biomass to similar efficiency as top performing conventional ILs, such as [C$_2$C$_1$Im][OAc], but at much lower temperatures, and with less than half the IL normally required to be effective.

Results and Discussion

Compositional Analysis and Lignin Fractionation

The compositional analysis of switchgrass before and after pretreatment is summarized in Table 1. Solid recovery refers to the mass percentage of biomass (dry weight) recovered from the original biomass load. Three of the major plant cell wall components of switchgrass (i.e., glucan, xylan, and acid insoluble lignin), were monitored before and after the pretreatment. Untreated dry switchgrass contained 31.9% glucan, 20.2% xylan and 20.7% acid insoluble lignin. The pretreatment experiments were conducted at different conditions (i.e. 25° C. for 0.5, 1 and 3 hours; 50° C. for 0.5, 1 and 3 hrs). The solid recovery was decreased with increasing temperature and time. By using the conditions of 50° C. for 3 hrs, approximately 48 wt % of the biomass was recovered, of which 62% was glucan, 12.7% was xylan and 10.5% was lignin. Based on the compositional change, the mass loss is caused by significant removal of lignin, xylan, and/or other soluble extractives. While the loss of glucan was approximately 6.5 wt %, the removal of xylan was significantly higher (~69.8 wt %). Also, the lignin removal during pretreatment process (~75.7 wt %) was comparable with our previous results for switchgrass with 49-87% lignin removal after pretreatment with different types ILs at high temperature (140° C.). [Sun N, et al., *Green Chemistry.* 2014; 16(5): 2546-2557].

TABLE 1

Compositional analysis[a] of pretreated switchgrass and the removal of the major components

| Temp./time (° C./h) | Solid recovery | Composition of pretreated biomass | | | Removal[c] of the major components | | |
|---|---|---|---|---|---|---|---|
| | | glucan % | xylan % | Lignin[b] % | glucan % | xylan % | Lignin[b] % |
| / | / | 31.9 ± 0.1 | 20.2 ± 0.1 | 20.7 ± 0.1 | / | / | / |
| 25/0.5 | 71.3 ± 0.5 | 43.8 ± 0.6 | 19.2 ± 0.1 | 16.1 ± 0.1 | 2.2 | 32.2 | 44.7 |
| 25/1 | 68.5 ± 0.5 | 45.5 ± 1.0 | 18.8 ± 0.4 | 16.5 ± 0.8 | 2.3 | 36.2 | 46.2 |
| 25/3 | 65.2 ± 0.4 | 47.7 ± 0.3 | 18.2 ± 0.1 | 13.0 ± 0.1 | 2.4 | 41.1 | 59.0 |
| 50/0.5 | 57.2 ± 0.5 | 54.4 ± 0.2 | 16.6 ± 0.2 | 13.8 ± 0.1 | 2.5 | 53.0 | 62.0 |
| 50/1 | 51.0 ± 0.3 | 59.5 ± 0.6 | 15.9 ± 0.3 | 12.4 ± 0.2 | 4.3 | 59.8 | 69.6 |
| 50/3 | 48.1 ± 0.4 | 62.0 ± 0.6 | 12.7 ± 0.1 | 10.5 ± 0.3 | 6.5 | 69.8 | 75.7 |

[a]The calculation is based on biomass dry weight;
[b]acid-insoluble lignin;
[c]removal of the major components is calculated based on compositions of raw switchgrass.

Cellulose Crystallinity

X-ray diffraction (XRD) studies were conducted to determine the changes in the crystalline vs. non-crystalline components (i.e. amorphous cellulose, hemicellulose and lignin) found in the switchgrass sample, and to monitor the structural changes in these polymers that occur during [TBA][OH] pretreatment. Commercial Avicel was used as cellulose standard to validate the results. Further, components isolated from the pretreatment condition (50° C. for 3 hrs) were utilized for cellulose crystallinity and lignin characterization studies.

Figure 7:
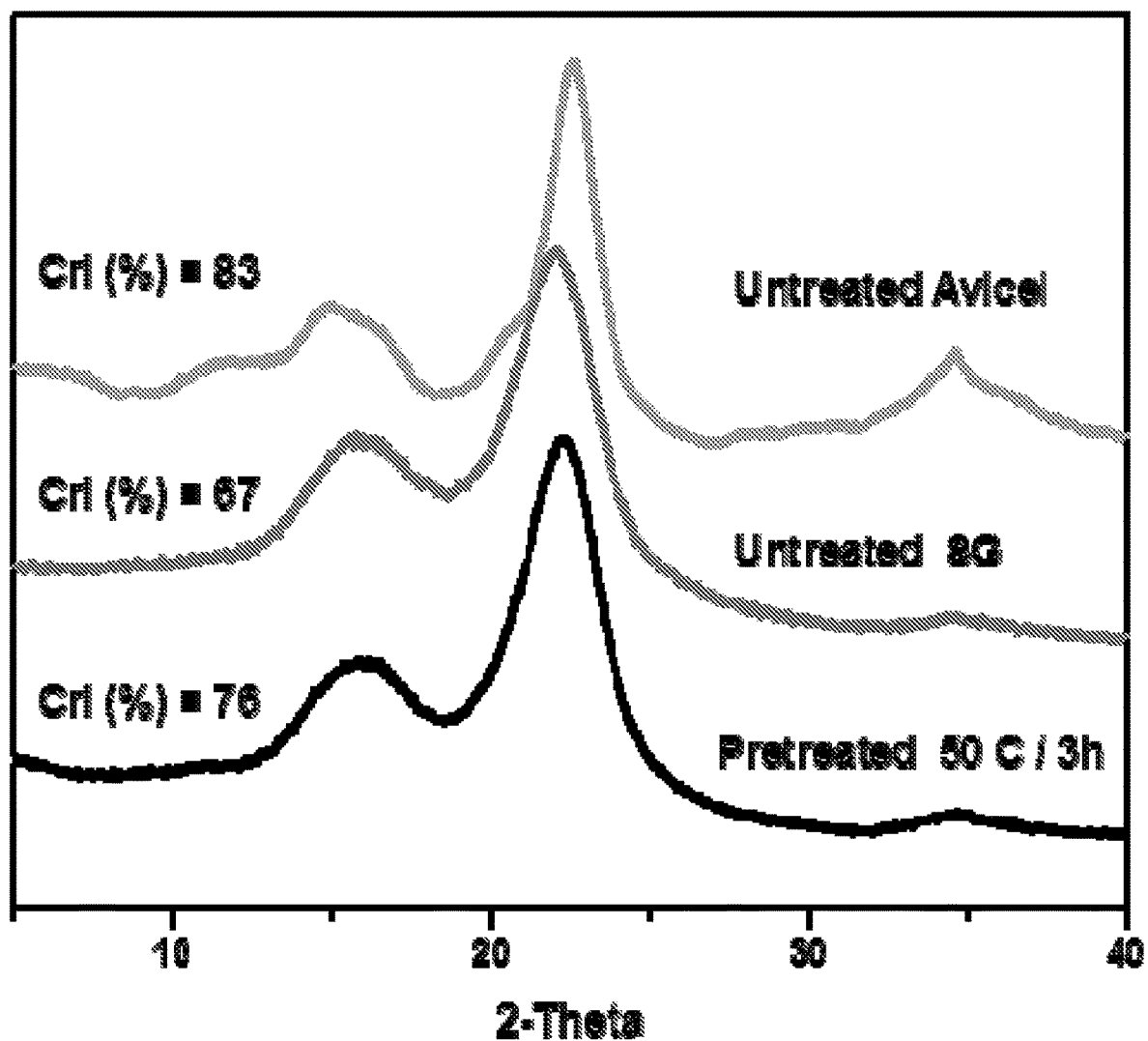
FIG. 7. X-ray diffraction patterns and CrI (%) values of untreated Avicel, switchgrass solids and pretreated switch grass by [TBA][OH] at 50° C. pretreatment conditions.

FIG. 7 shows the X-ray diffractograms of the untreated and pretreated switchgrass after processing at 50° C. for 3 hrs. The diffractogram obtained from the untreated switchgrass has two major diffraction peaks at 22.50 and 15.70° 2θ, characteristic of the cellulose I polymorph that corresponds to [002] and combined [101]+[10$\bar{1}$] lattice planes, respectively. The third small peak at 34.5° ([040] lattice plane) corresponds to ¼ of the length of one cellobiose unit and arises from ordering along the fiber direction. [Cheng G, et al., *The Journal of Physical Chemistry B.* 2012; 116(33): 10049-10054; Mansikkamäki P, Lahtinen M, Rissanen K., *Cellulose.* 2005; 12(3): 233-242; Park S et al., *Biotechnol Biofuels.* 2010; 3(10)] Obtained crystallinity index from the XRD patterns of the pretreated switch grass indicates that the low temperature pretreatment based on 40 wt % [TBA][OH] has minimal impacts on cellulose. Although the diffractogram obtained from switchgrass pretreated with [TBA][OH] still retains the cellulose I polymorph, a small shift is observed in all three peaks. The diffractogram obtained from switchgrass pretreated with [TBA][OH] still retains the cellulose I polymorph with a realignment of [002] peak with Avicel indicating removal of amorphous cell wall components such as lignin and hemicellulose. [Sun N, et al., *Green Chemistry.* 2014; 16(5): 2546-2557; Socha A M, et al., *Proceedings of the National Academy of Sciences.* 2014; 111(35): E3587-E3595] This also reflected in the increase in the crystallinity index (CrI) of switchgrass from 67% to 76% after pretreatment.

Sugar Yields

The sugar yields are calculated based on the glucan or xylan present in the original biomass (converting pretreated biomass to original using the solid recovery data in Table 1). As shown in Table 2, pretreatment using [TBA][OH] at 50° C. followed by saccharification generated high glucose yields of 93.1% after 3 hrs, and pretreatment at 25° C. generated glucose yields of 72.2% (0.5 hr) to 76.9% (3 hrs). Longer pretreatment times resulted in better glucose yields for both temperatures. Regardless of operating time, a higher xylose yield after saccharification was obtained at the lower temperatures studied, and is attributed to more hemicellulose being present in the recovered solids after pretreatment. The enhancement of sugar yields at the lower temperature aqueous [TBA][OH] IL pretreatment is primarily due to the removal of hemicellulose and lignin. The results indicate that an aqueous solution of 40 wt % [TBA][OH] solution is efficient for the pretreatment of switchgrass at mild conditions. In addition, the recyclability of [TBA][OH] in biomass dissolution has been demonstrated recently. [Zhong C et al, *Carbohydrate Polymers*. 2013; 94(1): 38-45] Using the conditions (e.g. 50° C., vacuum degree 0.1 MPa), it is expected that after lignin filtration, TBA][OH] could be generated and reused for next run.

TABLE 2

Glucose and xylose yields after enzymatic saccharification of the pretreated switchgrass

| Temp.[a] (° C.) | Time/h | Glucose yield[c] (%) | stdev | Xylose yield[c] (%) | stdev |
|---|---|---|---|---|---|
| 25[b] | — | 15 | 2.0 | 10.0 | 2.0 |
| 25 | 0.5 | 72.2 | 0.1 | 31.2 | 0.1 |
| 25 | 1 | 76.2 | 0.2 | 36.4 | 0.1 |
| 25 | 3 | 76.9 | 0.3 | 34.3 | 0.1 |
| 50 | 0.5 | 85.6 | 0.3 | 26.4 | 0.1 |
| 50 | 1 | 86.7 | 0.6 | 28.1 | 0.1 |
| 50 | 3 | 93.1 | 2.54 | 20.6 | 1.34 |

[a]pretreatment temperature;
b: untreated original biomass;
[c]calculation is based on the glucan or xylan present in the original biomass.

Lignin Characterization

Figure 8:
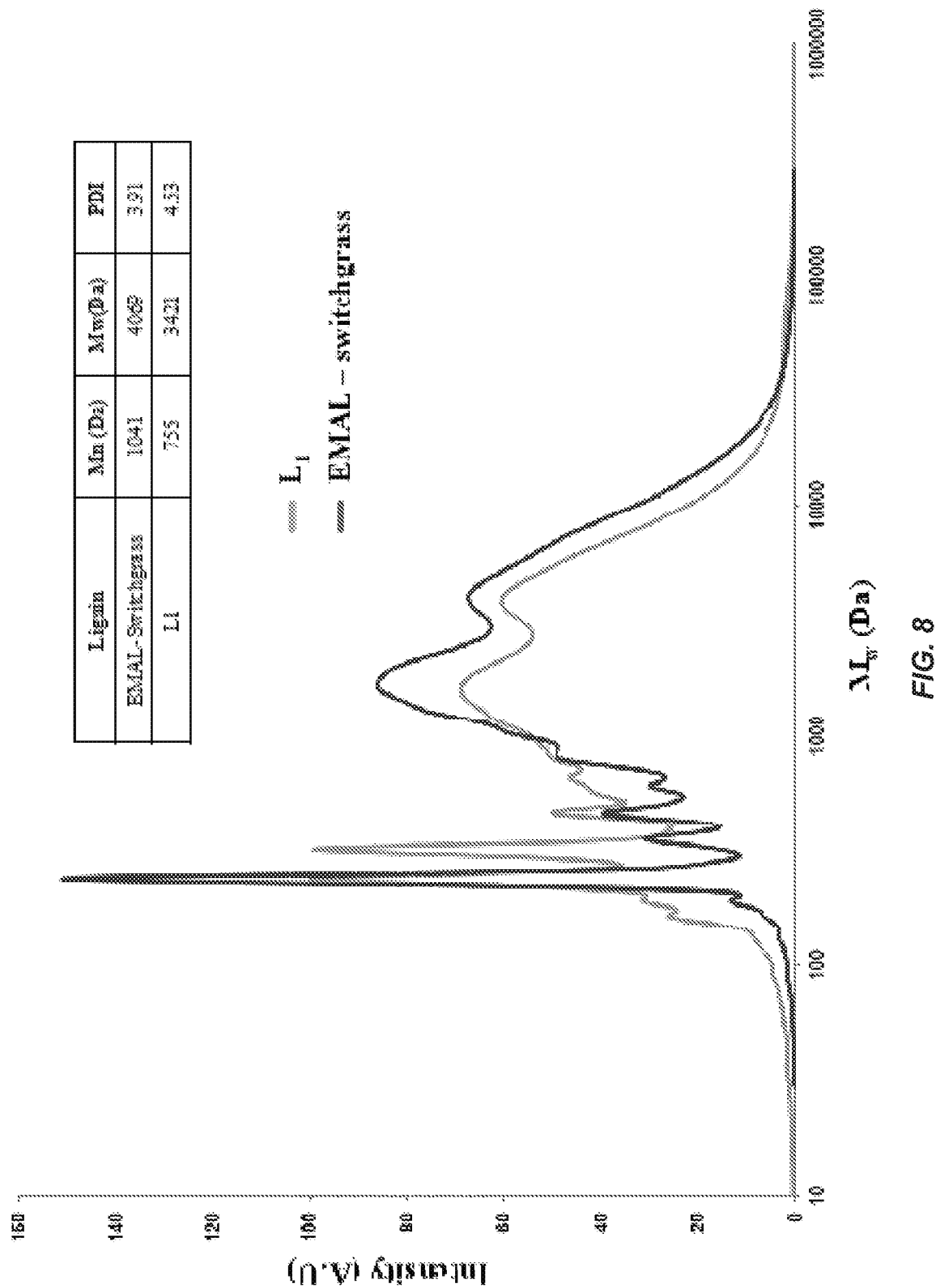
FIG. 8. Normalized SEC chromatograms of EMAL-switchgrass and $L_1$.

In order to examine the effect of [TBA][OH] pretreatment process on lignin, we carried out detailed lignin characterization studies using size exclusion chromatography (SEC) and 2D $^{13}$C-$^{1}$H HSQC NMR techniques. The lignin solubilized in the [TBA][OH] after pretreatment ($L_1$) was isolated by adjusting the pH to 2-3. The isolated lignin was compared with enzymatic mild acid lignin (EMAL) extracted from switchgrass, as it is commonly believed to be a close representation of the 'native' switchgrass lignin. The EMAL lignin from switchgrass was isolated based on the procedure reported by Wu and Argyropoulos. [Wu S, Argyropoulos D, *Journal of Pulp and Paper Science*. 2003; 29(7): 235-240] The elution profiles acquired by monitoring UV absorbance (X=280 nm) from SEC measurements of EMAL and the lignin isolated from the liquid stream ($L_1$) are depicted in FIG. 8. Although, the main elution peaks (Mw=1.0-10.0 kDa) for both EMAL and $L_1$ are comparable, a through comparison in the higher molecular weight region (Mw>10.0 kDa) region shows that $L_1$ has slightly lower molecular weight than EMAL, indicating small reduction of size. Apart from that, $L_1$ shows greater low molecular weight tails (Mw>1.0 KDa) along with one new intense low molecular weight peak (Mw=322 Da), both these observations indicate more abundant lower molecular weight lignin fractions as compared to EMAL.

Figure 2:
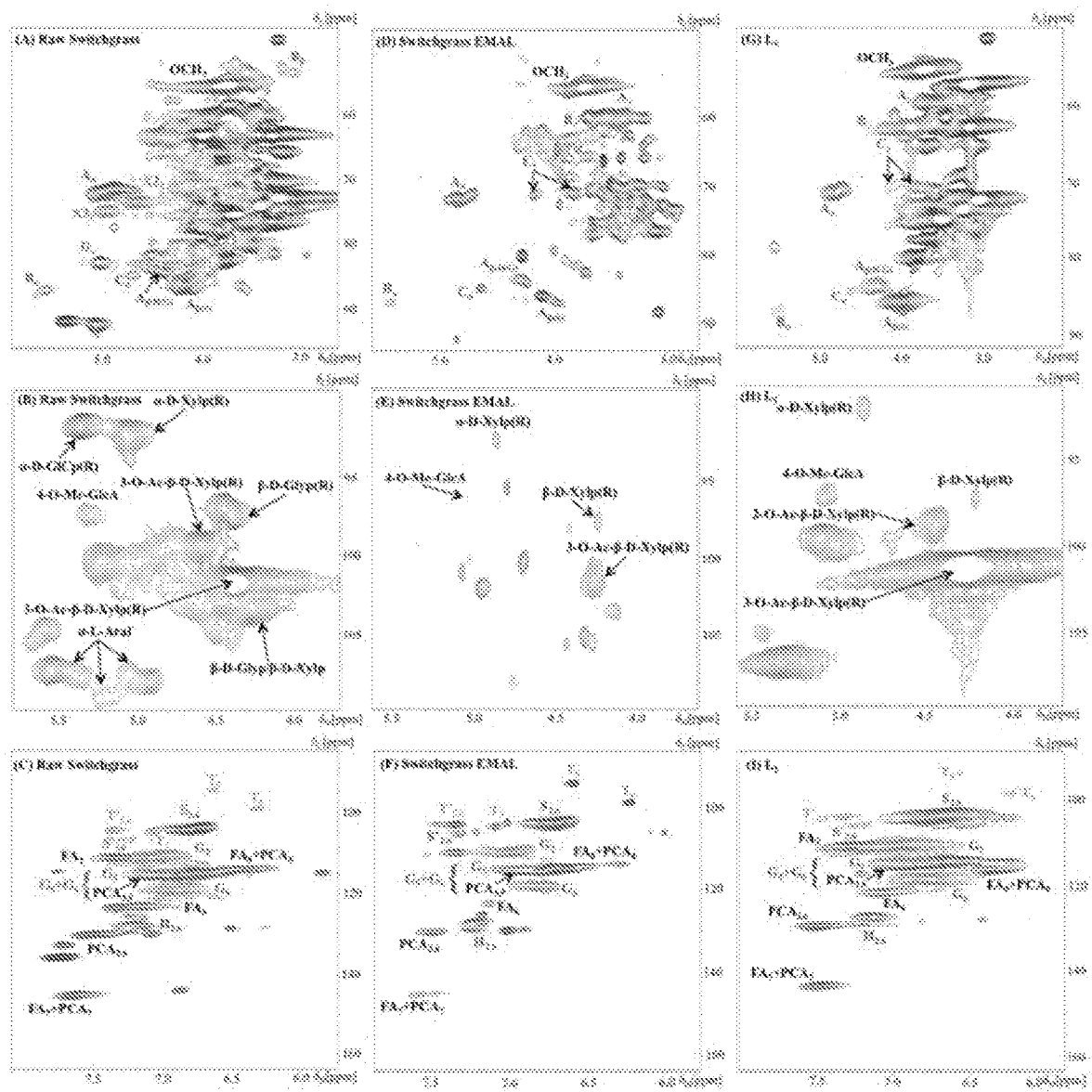
FIG. 2. 2D HSQC NMR spectra of aliphatic regions of untreated switchgrass (A), EMAL (D) and $L_1$(G); anomeric regions of untreated switchgrass (B), EMAL (E) and $L_1$ (H); and aromatic regions of untreated switchgrass (C), EMAL (F) and $L_1$(I).

To understand the structural changes that occur in lignin during the pretreatment process, the isolated lignin was compared with EMAL and raw switchgrass using 2D $^{13}$C-$^{1}$H heteronuclear single quantum coherence (HSQC) nuclear magnetic resonance (NMR) (FIG. 2). The cross peaks were assigned according to standards reported in the literature. [Bunzel M, Ralph J, *Journal of agricultural and food chemistry*. 2006; 54(21): 8352-8361; Ibarra D, et al., *Holzforschung*. 2007; 61(6): 634-646; Ibarra D, et al., *Journal of agricultural and food chemistry*. 2007; 55(9): 3477-3490; Kim H, Ralph J., *Organic & biomolecular chemistry*. 2010; 8(3): 576-591; Kim H, Ralph J, Akiyama T., *BioEnergy Research*. 2008: 1(1): 56-66; Thygesen A et al., *Cellulose*. 2005; 12(6): 563-576; Yelle D J, Ralph J, Frihart C R, *Magnetic Resonance in Chemistry*. 2008; 46(6): 508] The structures in these HSQC spectra correspond to the color-coded structures depicted in FIG. 9. Lignin side chains and interunit correlations are shown in aliphatic (top row, FIG. 2A) and aromatic regions (bottom row, FIG. 2C) and the polysaccharides are shown in the anomeric region (middle row, FIG. 2B). The relative changes in the lignin chemical structures were determined based on the volume integrations of HSQC spectral contour correlations. The HSQC spectrum of the cell wall of the untreated switchgrass shows that the β-aryl ether interunit linkages ($A_\alpha$, $A_{\beta(H/G)}$, $A_{\beta(S)}$, substructure A) are the predominant linkages in the lignin with small contributions of phenylcoumaran (β-5, substructure B), resinol (β-β, substructure C), and dibenzodioxocin (substructure D) linkages. The aliphatic region also exhibits two distinct peaks of 2-O-Ac-β-D-Xylp(R) ($X2_2$) and 3-O-Ac-β-D-Xylp (R) ($X3_3$) that represent major acetylated components of hemicelluloses. The aromatic region of the cell wall of the raw switchgrass indicates the lignin is a S/G type lignin with a minor amount of H-type lignin containing p-coumarates (pCA) and ferulates (FA), which is consistent with previous literature reports. [Bunzel M, Ralph J, *Journal of agricultural and food chemistry*. 2006; 54(21): 8352-8361; Kim H, Ralph J., *Organic & biomolecular chemistry*. 2010; 8(3): 576-591: Kim H, Ralph J, Akiyama T., *BioEnergy Research*. 2008; 1(1): 56-66; Yelle D J, Ralph J, Frihart C R, *Magnetic Resonance in Chemistry*. 2008: 46(6): 508] The HSQC spectrum of the untreated switchgrass also shows the presence of tricin moieties (substructure T).

Figure 9:
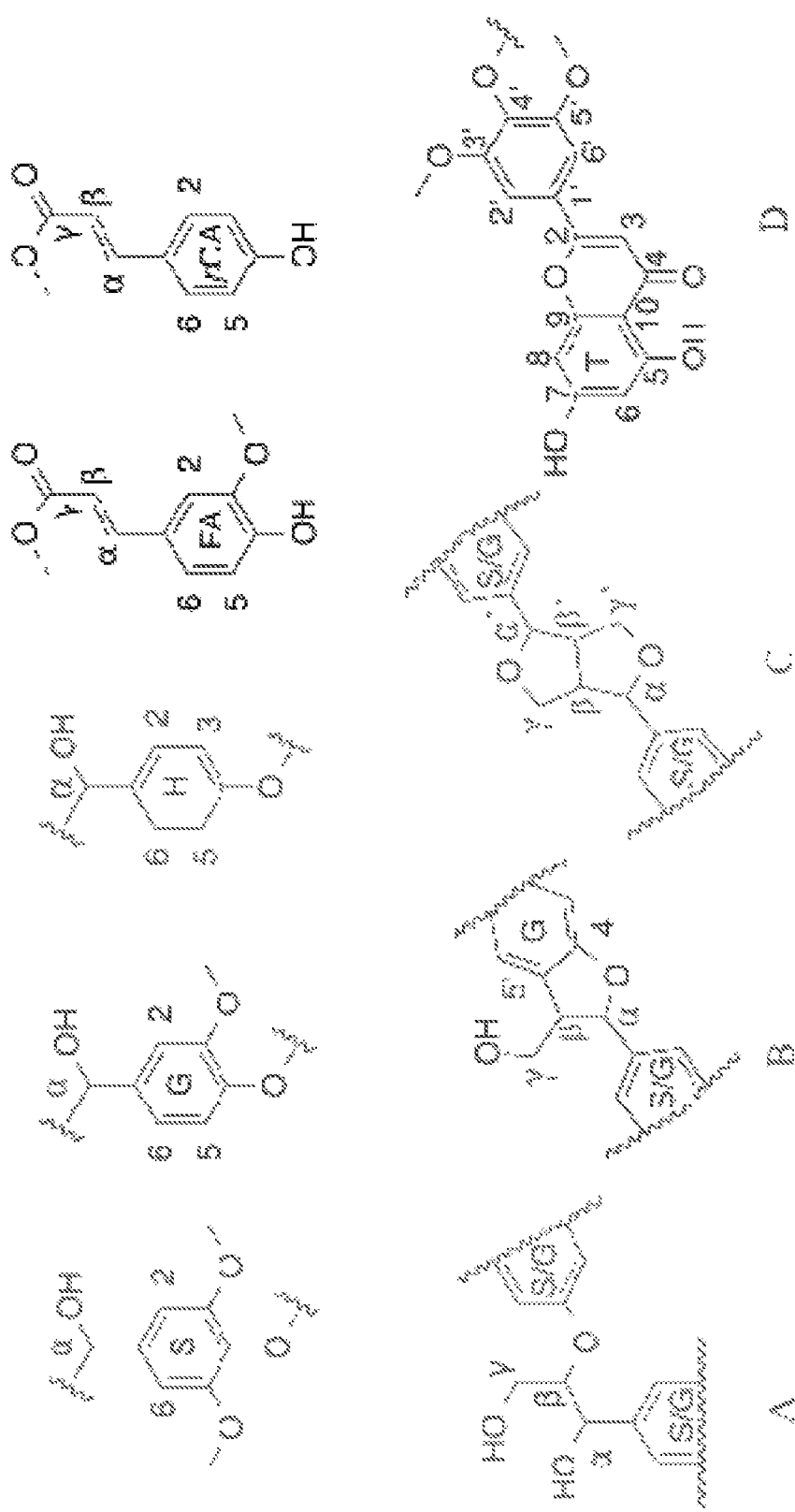
FIG. 9. HSQC spectra correspond to the color coded substructures.

The HSQC spectrum of $L_1$ is shown in FIGS. 2 (G-I). The weaker signal intensity of the $A_\square$ interunit linkages suggest chemical changes in the β-aryl ethers during the [TBA][OH] pretreatment. The absence of dibenzodioxocin signal (SC/ 8H: 83.3/4.81 ppm) indicates that the lignin isolated from the liquid stream is more linear as compared to the branched lignin in the untreated switchgrass due to removal of the points of branching. [Argyropoulos D S, et al., *Journal of agricultural and food chemistry*. 2002; 50(4): 658-666] Additionally, the absence of $X2_2$ and $X3_3$ correlations suggests deacetylation of hemicellulose occurred more readily at $C_2/H_2$ position. The anomeric regions of the untreated biomass and $L_1$ demonstrates a noticeable decrease of α-D-Glcp(R)/α-D-Xlyp(R) may be due to glycosidic bond cleavage and reduction in the degree of polymerization (DP) of hemicellulose during [TBA][OH] pretreatment. When compared with the switchgrass EMAL (FIGS. 2D-F), $L_1$ has similar interunit traits in both aliphatic and aromatic regions of the HSQC spectra. The relative abundance of different interunit linkages in EMAL and $L_1$ is shown in FIG. 9. In $L_1$, the β-aryl ether interunit linkages decrease from 59% to 43% as compared to the EMAL, with a relatively smaller decrease in both phenylcoumaran and resinol substructures. This result is in agreement with the SEC results, confirming reduction of the lignin size due to depolymerization during [TBA][OH] pretreatment process. The absence of detectable dibenzodioxocin substructure suggests relatively linear lignin structure of both types of lignins. Tricin substructures were also detected in both EMAL and $L_1$. [Wen J-L et al., *Materials*. 2013; 6(1): 359-391] The SEC and 2D NMR studies suggested that $L_1$ has similar structure traits as switchgrass EMAL with a relatively smaller size. These results indicate that [TBA][OH] can very efficiently solubilize and partially depolymerize the lignin present in switchgrass.

Glycome Profiling

Figure 3:
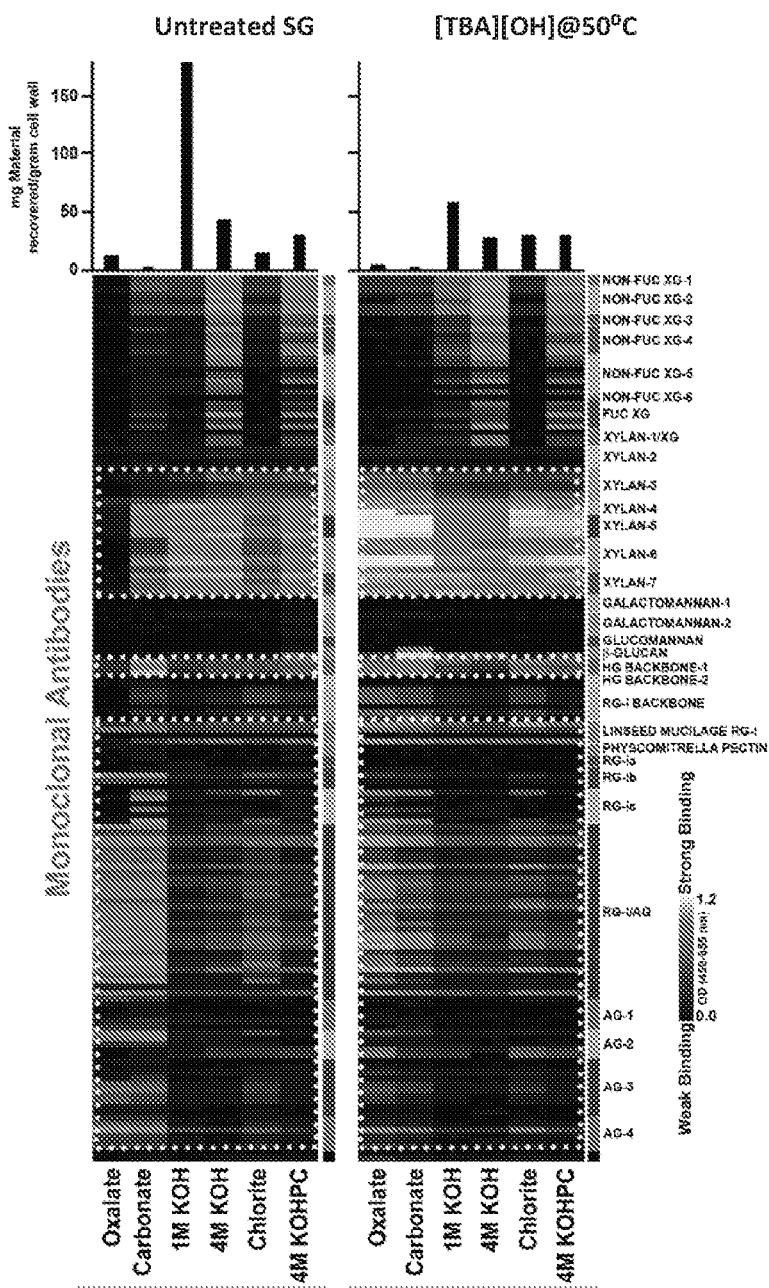
FIG. 3. Glycome profiling of untreated switchgrass, and switchgrass pretreated with [TBA][OH] at 50° C. for 3 hours: Sequential cell wall extracts (bottom) were subjected to ELISA screens with monoclonal antibodies for most major non-cellulosic plant glycan classes (right). The ELISA binding response values are represented as a color-coded "heatmap" (center) and the recovered masses of carbohydrate material resulting from each extraction step is represented with bar graphs (top).

Glycome profiling of untreated and [TBA][OH] pretreated switchgrass biomass was conducted to facilitate a comparative study of the overall changes in composition and extractability patterns of the major non-cellulosic cell wall glycans. Concomitantly, the results from glycome profiling analyses were employed to understand how [TBA][OH] pretreatment cause reduced cell wall recalcitrance in switchgrass. Glycome profiles of untreated and [TBA][OH] pretreated switchgrass at 50° C., as depicted in FIG. 3, revealed significant differences that are highlighted in the yellow dotted blocks. These significant differences in the glycome profiles of pretreated biomass indicate that pretreatment regime caused an overall change in cell wall structure, architecture and composition. In general, [TBA][OH] pretreated switchgrass exhibited lesser amounts of materials recovered (see bar graphs on top panel) in all base extracts (1M KOH, 4M KOH and 4M KOHPC) hinting at the removal and fragmentation of potentially non-cellulosic cell wall components (that may also include hemicelluloses) during the [TBA][OH] pretreatment process. Interestingly, prominent variations were observed in the abundances of non-cellulosic glycan epitopes in oxalate and carbonate extracts from pretreated biomass samples in comparison to the untreated biomass. For instance, a considerably higher abundance of xylan epitopes (as indicated by the higher binding of xylan-3 through xylan-7 groups of mAbs that recognize both un-substituted and substituted xylans) was observed in oxalate and carbonate extracts from [TBA][OH] pretreated switchgrass at 50° C. that indicates enhanced xylan extractability. As previous studies have noted, such enhanced extractability of xylan epitopes is indicative of structural changes in the cell walls that results in reduced recalcitrance. [Pattathil S, et al., *Industrial Biotechnology*. 2012; 8(4): 217-221]

Substantial differences in patterns of extractabilities of epitopes of pectic-components were also observed between the untreated and [TBA][OH] pretreated switchgrass. For example, oxalate extracts from [TBA][OH] pretreated samples showed significantly higher abundance of pectic backbone epitopes (as indicated by the higher binding of homogalacturonan backbone-1 and rhamnogalacturonan-I groups of mAbs). Pectic-arabinogalactan and arabinogalactan epitopes (as indicated by the binding of RG-I/AG and AG groups of mAbs) were highly abundant in oxalate and carbonate extracts from untreated switchgrass, however, this abundance decreased in [TBA][OH] pretreated switchgrass samples (potentially due to enhanced glycan fragmentation). The chlorite extraction step employed in sequential extraction breaks up and removes lignin to release any lignin-associated polysaccharides into the extract. Chlorite extracts from pretreated switchgrass under [TBA][OH] at 50° C. conditions contained higher abundance of xylan epitopes as compared to untreated samples indicating ILs perturbing effect on potential lignin-xylan associations. Overall, glycome profiling studies revealed the major structural modifications induced by [TBA][OH] at the mild pretreatment condition on switchgrass biomass resulted in efficient hydrolysis of cellulose to its constituent sugars.

Computational Modeling

Figure 4:
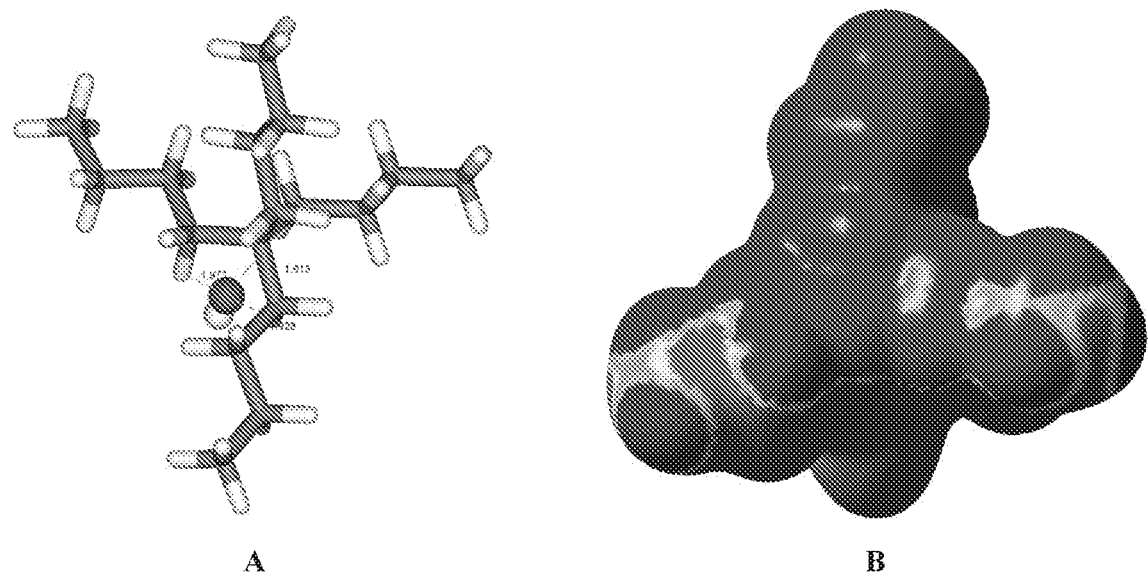
FIG. 4. (a) Optimized geometry indicating anion cation association (b) molecular electrostatic potential map of [TBA][OH] at the +0.04 au isosurface. The color scale indicates the charges on the atoms: red=most negative, green=neutral, blue=most positive charge.

To understand the molecular level forces on the biomass dissolution at low temperature using [TBA][OH], the first requirement is to determine the chemical nature of [TBA] [OH] that solubilizes lignocellulose. The optimized molecular geometry of [TBA][OH] obtained using hybrid density functional theory (DFT) calculations is shown in FIG. 4. The most stable conformation arises from interactions of an oxygen atom of the [OH]$^-$ with the ionic region around nitrogen atom in [TBA]$^+$. Due to the short $O_{OH}\cdots H-C_{TBA}$ bond distances (1.91-1.97Å) allowing strong intermolecular interaction energy (IE) (116.8 kcal/mol) between cation and the anion of [TBA][OH]. It is clearly seen from the depicted molecular electrostatic potential (MESP) map of [TBA] [OH] that the distinct separation of positive (blue) and negative regions (red) play a dominant role by influencing strong ionic interactions, electrostatics, and hydrophobic interactions with biomass components. [Medronho B, Lindman B, *Current Opinion in Colloid & Interface Science*. 2014; 19(1): 32-40]

Figure 5:
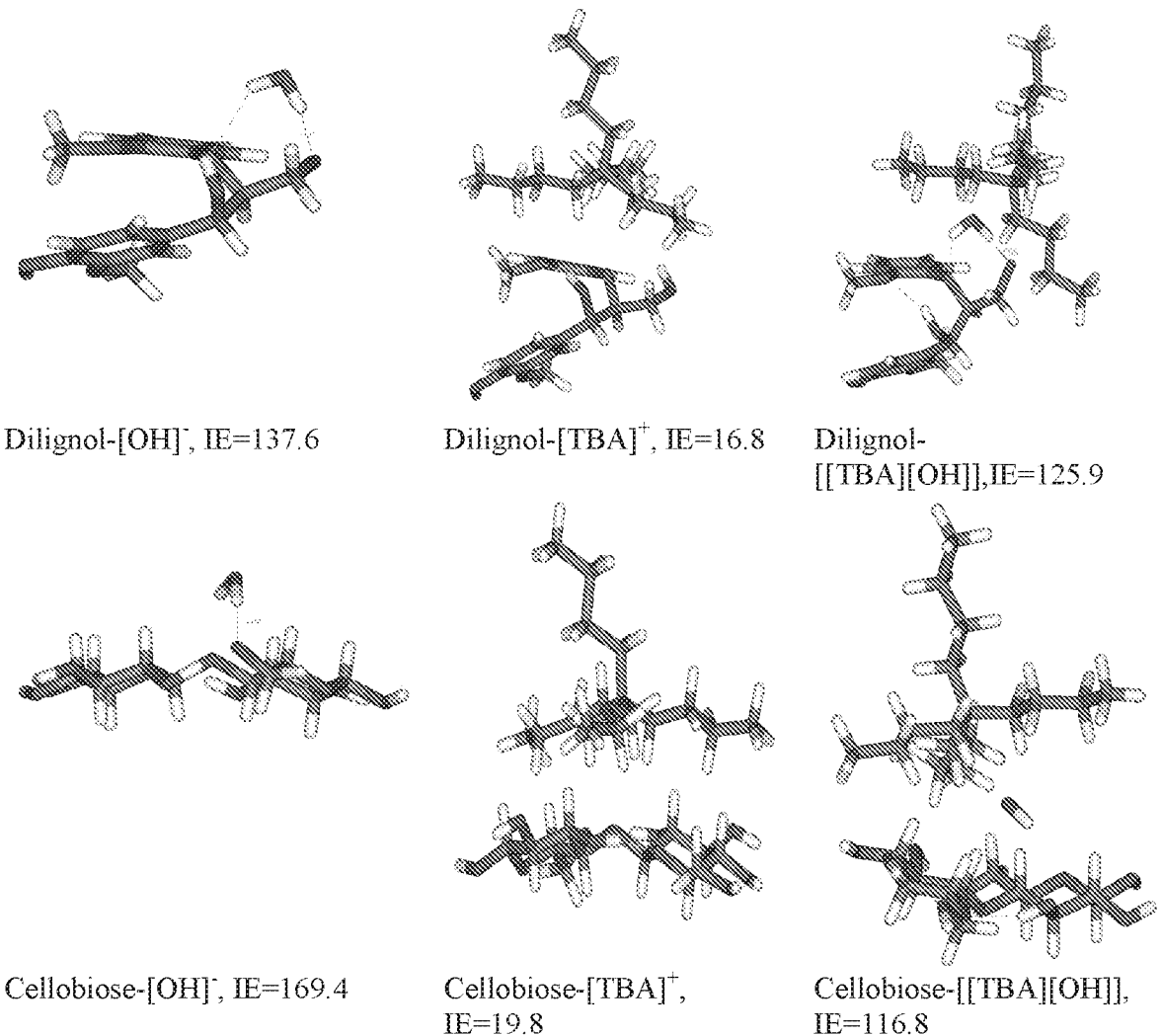
FIG. 5. Optimized geometries of dilignol and cellobiose with [OH], [TBA]f and [TBA][OH]. Interaction energy (IE) is reported in kcal/mol.

We evaluated the influence of the anion and cation interactions on biomass dissolution by performing quantum chemical calculations of [OH]$^-$, [TBA]$^+$ and [TBA][OH] interacting with a model dilignol and cellobiose compounds (FIG. 5). From the calculated IEs, it was found that [OH]$^-$ interacts with dilignol and cellobiose more strongly than [TBA]$^+$ cation, and the IE of [OH]$^-$ with cellobiose is slightly higher than that of its interactions with dilignol. In the case of [TBA]$^+$ interactions, our calculations show a slightly higher IE for cellobiose than for dilignol, which are most probably due to hydrophobic interactions. Interestingly, IE strength of ion-pair complexes with biomass components are more favored toward dilignol than cellobiose. This trend agrees with the experimental observation on lignin removal and provides insights on [TBA][OH] interactions with biomass components. Previous experimental studies [Zhong C et al, *Carbohydrate Polymers*. 2013; 94(1): 38-45] on [TBA][OH] that have been carried out on cellulose show strong contact with cellulose in the absence of any other competing biomass compounds (i.e. lignin). Considering the components in whole biomass, interactions with [TBA][OH] reveal that this IL has more affinity with lignin and thus enables higher amount of lignin removal. Delignification of [TBA][OH] enhances the cellulose accessibility for enzymatic digestion. Another important point to note is that [TBA][OH] interactions could also account for biomass permeability as a result of the large amount of xylan removal by the [OH]$^-$, since these types of bases are known to involve reactions under mild conditions. [Kumar P, Barrett D M et al., *Industrial & Engineering Chemistry Research*. 2009; 48(8): 3713-3729] It has been reported that alkaline ions could instigate the progression of following steps involving (i) cellulose swelling; (ii) internal surface area enhancement; (iii) changes in cellulose crystallinity; (iv) hemicellulose removal; (v) reducing the lignin and carbohydrate association and (vi) disrupting the lignin structure by breaking its glycosidic ether bond. Hence, lignin cannot further act as a protective shield to the cellulose after lignin dissolution, consequently making cellulose more susceptible for degradation.

Figure 10:
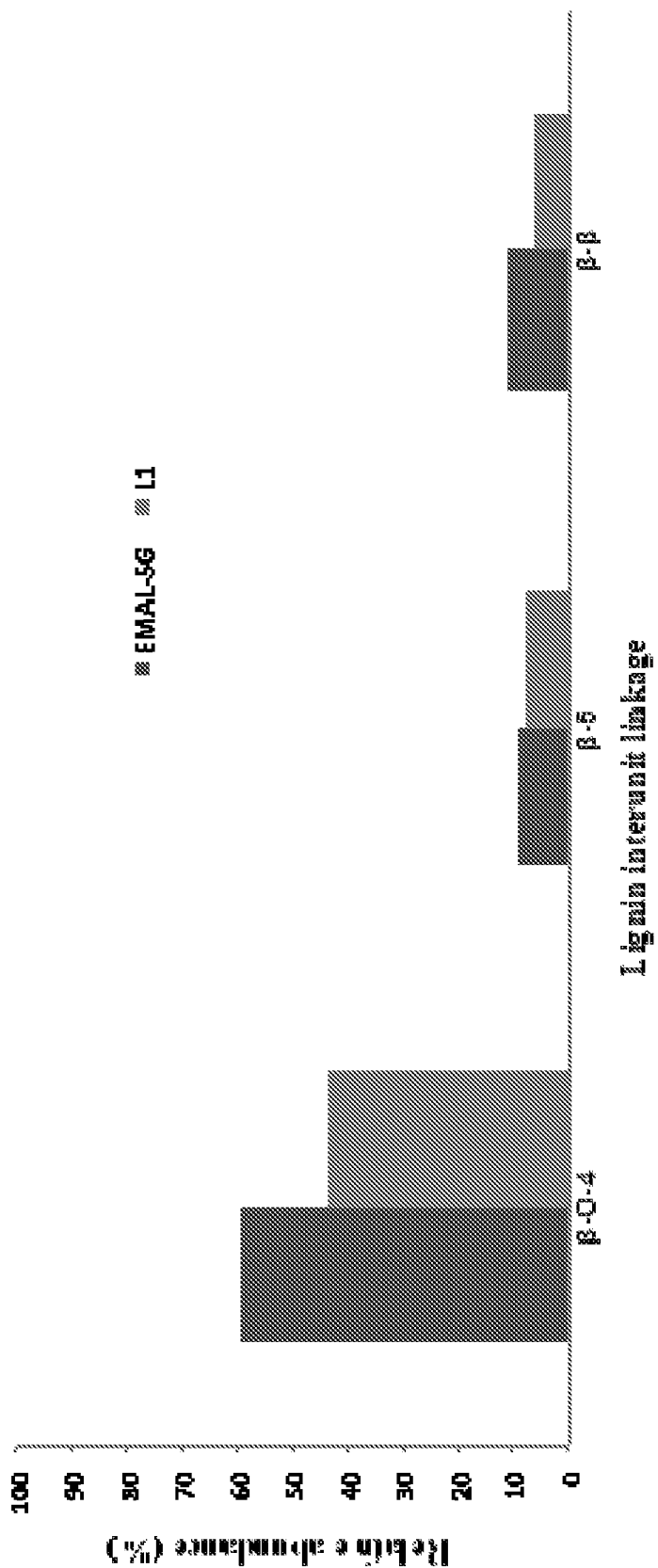
FIG. 10. Relative abundances in lignin interunit linkages in switchgrass EMAL and $L_1$.
Figure 11:
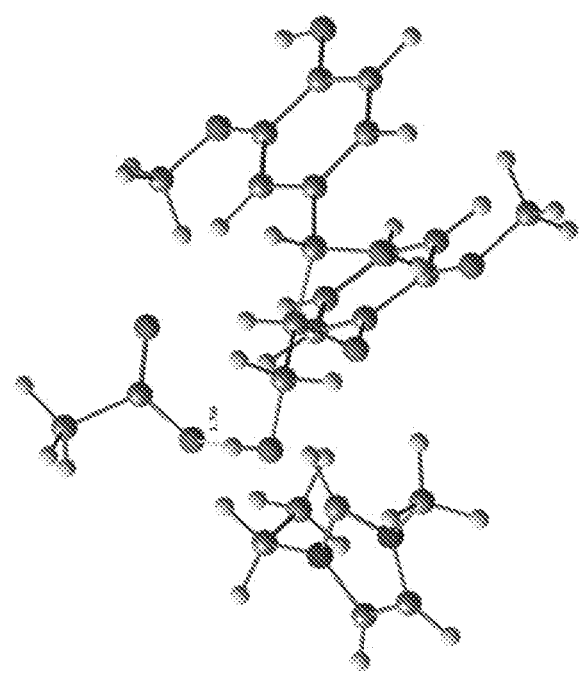
FIG. 11. Optimized geometries of dilignol with IL complexes.
Figure 11:
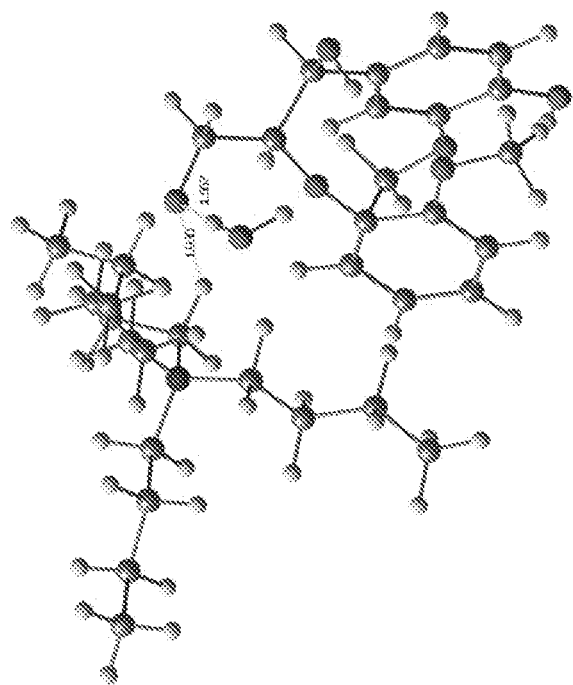

We then sought to determine what properties and interactions are dominant at these lower temperatures. Ionic conductivity, ion mobility, and viscosity of ILs are the key factors and vary based on ion type, size, charge, and temperature. [MacFarlane D R, Seddon K R, *Australian journal of chemistry*. 2007; 60(1): 3-5] The higher pH (~14) of [TBA][OH] significantly influences the lignin removal. [Pedersen M, Meyer A S, *New Biotechnology*. 2010; 27(6): 739-750] The low temperature mechanism of biomass dissolution is particularly dependent on the ion exchange and contribution from ionic interactions between the biomass and ILs. Optimized geometries of lignin with [$C_2C_1$Im][OAc] and lignin with [TBA][OH] (FIG. 10) are analyzed more carefully. It is interesting to point out that the proton/hydrogen exchange from the dilignol to [OH] anion has seen for the [TBA][OH]-lignin complexes. On the other hand, no significant elongation was observed for the O—H group of the lignin interacting with [OAc]⁻ of [$C_2C_1$Im][OAc]-lignin complexes. This ion mobility of [OH]⁻ enhances the ionic conductivity, and the [$C_2C_1$Im]⁺ is involved in stabilizing the complexes. Therefore, [TBA][OH] is more reactive than the other ILs used in pretreatment at higher temperature in terms of ionic interactions that extends their solvation capability at the lower temperature. Higher temperature conditions could manipulate these solvation properties for other ILs with different anions and cations. More importantly, ion pair type, size, charge, and co-solvents can be modified to design ILs with effective ionic conductivity and viscosity [Cruz H et al., *Chemical Communications*. 2012; 48(45): 5620-5622] for the efficient biomass dissolution under mild conditions.

Process Modeling and Energy Demand Analysis on Low Temperature IL Pretreatment

Figure 6:
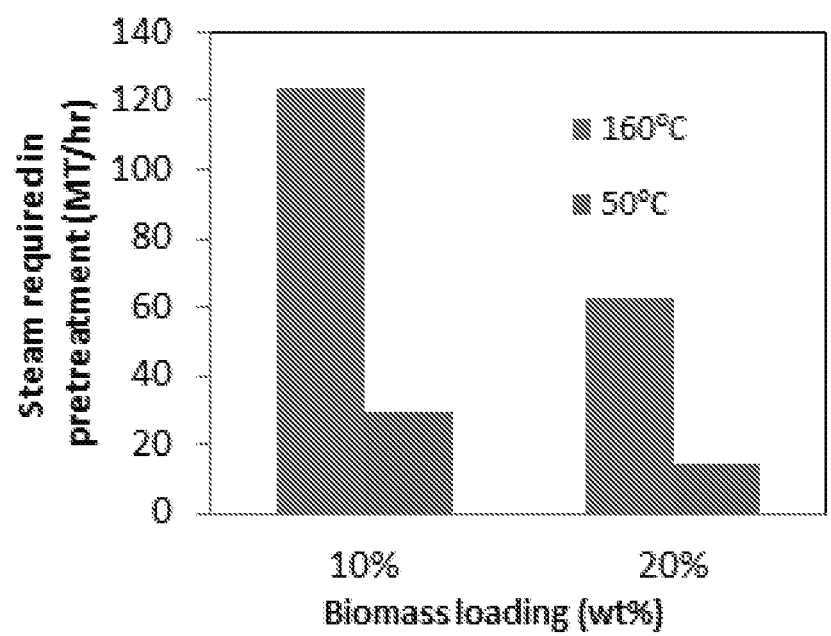
FIG. 6. Impact of the temperature on energy requirement in the pretreatment process at industrial scale (to process 2000 MT/day dry biomass).

One important consideration for the developed pretreatment for [TBA][OH] is lower temperature process. To understand the impact of [TBA][OH] based low temperature pretreatment demonstrated in this study on the energy requirement, a process model was developed in SuperPro Designer (v8.5). The process consists of a pretreatment reactor and the performance of [TBA][OH] pretreatment process, in terms of energy intensity, is benchmarked against a more conventional [$C_2C_1$Im][OAc] process. The [TBA][OH] pretreatment was carried out at 50° C. while the [$C_2C_1$Im][OAc] pretreatment was conducted at 160° C. Physical properties of the ILs (such as heat capacity) were collected from the literature. [Bhatt V D, Gohil K. Performance evaluation of solar cooker using some [N] based ionic liquids as thermal energy storage materials] Overall, four scenarios were constructed using these two ILs and two different biomass loadings (i.e., 10% and 20%). Energy demand calculations revealed more than 75% reduction in steam requirement during the low temperature pretreatment process to liberate carbohydrates with reduced energy input (FIG. 6). [Klein-Marcuschamer D, Simmons B A, Blanch H W, *Biofuels, Bioproducts and Biorefining*. 2011; 5(5): 562-569] As shown in the FIG. 6, the impact of pretreatment temperature on energy requirement is lower for [TBA][OH] in both biomass loading conditions compared to [$C_2C_1$Im][OAc]. This effort could potentially address the challenging issues of developing robust and energy efficient technologies for increasing the sugar yields at a lower cost from renewable, non-food lignocellulosic biomass

CONCLUSIONS

We have demonstrated the low temperature pretreatment of lignocellulosic biomass using the IL [TBA][OH] in the presence of water. The concept of inducing labile biomass deconstruction with reduced energy input and minimal IL loading has been successfully demonstrated. The effective pretreatment of 10 wt % switchgrass using aqueous mixtures of [TBA][OH] at 50° C. generated >90% glucose yields and outperformed current best IL pretreatment based on imidazolium ILs at similar severities. Process modeling and energy demand analysis has shown significant potential for reduction in the pretreatment energy requirement. For instance, this results in more than a 75% reduction in the steam requirement for [TBA][OH] compared to ILs that are used at temperatures above 140° C. Compositional analysis of the [TBA][OH] pretreated switchgrass show that the enhancement of sugar yields at lower temperatures is due to the removal of hemicellulose and lignin. Lignin characterization using SEC and NMR on the extracted lignin after pretreatment indicates that [TBA][OH] efficiently solubilizes and partially depolymerizes the lignin during pretreatment. DFT computations on chemical reactivity of [TBA][OH] and its interaction with cellobiose and lignin reveal that [TBA][OH] IL is more reactive than the imidazolium IL used in pretreatment at higher temperature in terms of ionic mobility which enables lignin removal at the lower temperature. Glycome profiling experiments provide evidence for significant removal of non-cellulosic components of biomass under mild [TBA][OH] pretreatment that is distinct from other ILs that require a higher temperature for better performance. By leveraging the benefits of ILs that are effective at very mild processing conditions, such as [TBA][OH], this study opens up an avenue for novel process designs that could significantly enhance the energy efficiency and affordability of the biorefinery by overcoming the temperature mismatch of pretreatment and saccharification unit operations.

Methods

Materials

Switchgrass (*Panicum virgatum*) was kindly provided from the laboratory of Prof. Daniel Putnam at the University of California, Davis. The switchgrass studied was a combination of lowland and upland varieties, grown in Davis, Calif. and harvested in 2011. The samples were ground using a Thomas-Wiley® Mill fitted with a 20-mesh screen (Model 3383-L10 Arthur H. Thomas Co., Philadelphia, Pa., USA) and used without further sieving. The samples were stored at 4° C. in a sealed plastic bag for use in all experiments. Commercial enzyme cocktails Cellic® CTec 2 and HTec 2 were generously provided by Novozymes (Davis, Calif.). The ILs [TBA][OH] (>95% purity) were purchased from Sigma-Aldrich.

Biomass Pretreatment

A 10% (w/w) biomass solution was prepared by combining 1 g of switchgrass with 9 g of IL in a 25 mL tube reactor. The reactor was heated in an oil bath to the desired temperature and stirred at 150 rpm with a magnetic stir bar for 3 h. All pretreatment reactions were conducted in duplicate. Following pretreatment, 30 mL of deionized (DI) water was slowly added to the biomass/IL slurry with continued stirring. The mixture was transferred to 25 mL Falcon tubes and centrifuged at high speed (14,000 rpm) to separate solids. The pretreated biomass was further washed with 2×30 mL of DI water to remove any residual IL. The solids were lyophilized and stored at 4° C. for analysis.

Compositional Analysis

Compositional analysis of switchgrass before and after pretreatment was performed using NREL acidolysis protocols (LAP) LAP-002 and LAP-005. Briefly, 200 mg of biomass and 2 mL 72% $H_2SO_4$ were incubated at 30° C. while shaking at 300 rpm for 1 h. The solution was diluted to 4% $H_2SO_4$ with 56 mL of DI water and autoclaved for 1 h at 121° C. The reaction was quenched by placing samples into an ice bath before removing the biomass by filtration. The filtrate was neutralized with $CaCO_3$ and monomeric sugars were determined from the filtrate by Agilent HPLC 1200 Series equipped with a Bio-Rad Aminex HPX-87P column and a Refractive Index detector (aqueous mobile phase, 0.6 mL/min, column temperature 85° C.). The injection volume was 10 µL with a run time of 25 min. Acid insoluble lignin was quantified gravimetrically from the solid after heating overnight at 105° C. (the weight of acid-insoluble lignin+ash) and then 575° C. for at least 6 h (the weight of ash).

Enzymatic Saccharification

Enzymatic saccharification of pretreated and untreated biomass was carried out using commercially available enzymes, Cellic® CTec2 and HTec2 from Novozymes, at 50° C., pH 5.5, and rotation speed of 150 rpm in a rotary incubator (Enviro-Genie, Scientific Industries, Inc.). All reactions were conducted at 10% biomass loading by placing 500 mg of biomass (dry weight) in a 25 mL centrifuge tube. The pH of the mixture was adjusted to 5.5 with 50 mM sodium citrate buffer (pH 4.8) supplemented with 0.02% NaN3 to prevent microbial contamination. The total reaction volume (5 mL) included a total protein content of 10 mg protein/g biomass (before pretreatment). The ratio of CTec2: HTec2 mixtures were held constant at 9:1 for all reactions. Reactions were monitored by centrifuging 50 µL aliquots of supernatant (5 min, 14,000 rpm) at specific time intervals and measuring monomeric sugar concentrations by HPLC as described previously.

X-Ray Diffraction (XRD)

The raw and pretreated biomass/Avicel were dried and characterized with powder X-ray diffraction (PXRD). The XRD analysis were performed on a PANalytical Empyrean X-ray diffactometer equipped with a PIXcel$^{3D}$ detector and operated at 45 kV and 40 kA using Cu Kα radiation (λ=1.5418 Å). The patterns are collected in the 2θ range from 5 to 60° with a step size of 0.039° and the exposure time of 300 seconds. A reflection-transmission spinner was used as a sample holder and the spinning rate was set at 8 rpm throughout the experiment. Crystallinity index (CrI) was determined by Segal's method. [Park S et al., *Biotechnology for biofuels*. 2010; 3(1): 1]

2D $^{13}C$-$^1H$ HSQC NMR Spectroscopy

Switchgrass cell wall and solids recovered from the liquid stream [TBA][OH] IL pretreatment via adjusting the pH were ball-milled, solubilized in DMSO-d6, and then analyzed by two-dimensional (2D) $^{13}C$-$^1H$ heteronuclear single quantum coherence (HSQC) nuclear magnetic resonance (NMR) as previously described. [Kim H, Ralph J., *Organic & biomolecular chemistry*. 2010; 8(3): 576-591] Briefly, ball-milled samples (~50 mg) were placed in NMR tubes with 600 µl DMSO-d6. The samples were sealed and sonicated until homogeneous in a Branson 2510 table-top cleaner Branson Ultrasonic Corporation, Danburt, Conn.). The temperature of the bath was closely monitored and maintained below 50° C. HSQC spectra were acquired at 398 K using a Bruker Avance-600 MHz instrument equipped with a 5 mm inverse gradient $^1H$/$^{13}C$ cryoprobe using the q_hsqcetgp pulse program (ns=64, ds=16, number of increments=256, d1=1.5 s). Chemical shifts were referenced to the central DMSO peak (δC/δH 39.5/2.5 ppm). Assignment of the HSQC spectra is described elsewhere. A semi-quantitative analysis of the volume integrals of the HSQC correlation peaks was performed using Bruker's Topspin 3.1 processing software.

Size Exclusion Chromatography (SEC)

The molecular weight distribution of lignin was investigated using a gel permeation chromatography (GPC). The lignin was acetylated with pyridine and acetic anhydride following a previously published procedure. [Ragauskas A, et al., *Frontiers in Energy Research*. 2014; 1] The acetylated lignin was dissolved in tetrahydrofuran (THF) with a concentration of 1 g/L. GPC analysis was performed using a Tosoh Ecosec HLC-8320 GPC equipped with a Refractive Index (RI) and Diode array detector (DAD) detector. Separation was achieved with an Agilent PLgel 5 µm Mixed-D column at 35° C. using a mobile phase of THF at a flow rate of 1.0 mL/min. The GPC standards, which contained polystyrene ranging from 162 to 29,150 g/mol, were purchased from Agilent and used for calibration. Absorbance of materials eluting from the column was detected at 280 nm (UV). The enzymatic mild acidolysis lignin (EMAL) process was used to extract lignin from switchgrass and it was used as a control.

Computational Details

The geometry optimizations of [TBA] cations and hydroxide anions, cellobiose, lignin dimer model (dilignol with β-O-4 linkage between two arene rings) were performed using density functional theory (DFT) with the M06-2X hybrid exchange-correlation functional and the 6-311++G(d, p) basis set. Frequency calculations were carried out to verify that the computed structures corresponded to energy minima. The most stable isolated cation/anion and their IL complexes obtained from our calculations are herein described. Several complexes of anions and cations interacting with cellobiose and dilignol (guided by the electrostatic potentials) were constructed and optimized at M06-2X/6-31G (d, p) basis set. The most stable complexes of cation and anion with cellobiose and dilignol were used to calculate interaction energies (IEs) at M06-2X/6-311++G(d, p) level using the supermolecular approach, $$IE = -\left(E_{Complex} - \sum_{i=1}^{n} E_i\right) \quad (1)$$

where $E_{Complex}$ refer to the energies of cation and anion pair (for IL), anion or cation with biomass components, anion and cation with biomass complexes, respectively and $E_i$ refer to the energies the monomers. The results were corrected for basis set superposition error (BSSE) following the procedure adopted by Boys and Bernardi. [Boys S F, Bernardi F., *Mol. Phys*. 1970; 19(4): 553-&] All quantum chemical calculations were performed using the Gaussian 09 suite of programs (Frisch M J, et al. (2009) Gaussian 09 (Gaussian, Inc, Wallingford, Conn.), Revision D.01.). [Gaussian 09 R A et al., Gaussian, Inc., Wallingford Conn., 2009]

Glycome Profiling

Glycome profiling of raw and [TBA][OH] IL pretreated biomass samples that involves preparation of cell walls [Alcohol Insoluble Residues (AIR)], sequential extractions of AIR were carried out as previously described. [DeMartini J D, et al., *Energy & Environmental Science*. 2011; 4(10): 4332-4339; Pattathil S et al., *Biomass Conversion*. Springer, 2012, pp 61-72] Plant cell wall glycan-directed monoclonal antibodies (mAbs) were from laboratory stocks (CCRC, JIM and MAC series) at the Complex Carbohydrate Research Center (available through CarboSource Services; http://www.carbosource.net) or were obtained from BioSupplies (Australia) (BG1, LAMP). Supporting information on mAbs

[Pattathil S, et al., *Plant physiology*. 2010; 153(2): 514-525] used in this study can be found in the Supplementary Information Table S1, including the link to WallMabDB (www.wallmabdb.net) that provides detailed information for each antibody.

Supplementary Material

A list of cell wall glycan-directed monoclonal antibodies (mAbs) used for glycome profiling analyses is provided in Table 3 below. The groupings of antibodies are based on a hierarchical clustering of ELISA data generated from a screen of all mAbs against a comprehensive panel of plant polysaccharide preparations that clusters mAbs according to the predominant polysaccharides that they recognize. The majority of listings link to the WallMabDB plant cell wall monoclonal antibody database (www.wallmabdb.net) that provides detailed descriptions of each mAb, including immunogen, antibody isotype, epitope structure (to the extent known), supplier information, and related literature citations.

TABLE 3

Glycan Groups and Antibodies that Specifically Bind

| Glycan Group Recognized | mAb Names |
| --- | --- |
| Non-Fucosylated Xyloglucan-1 | CCRC-M95 |
| | CCRC-M101 |
| Non-Fucosylated Xyloglucan-2 | CCRC-M104 |
| | CCRC-M89 |
| | CCRC-M93 |
| | CCRC-M87 |
| | CCRC-M88 |
| Non-Fucosylated Xyloglucan-3 | CCRC-M100 |
| | CCRC-M103 |
| Non-Fucosylated Xyloglucan-4 | CCRC-M58 |
| | CCRC-M86 |
| | CCRC-M55 |
| | CCRC-M52 |
| | CCRC-M99 |
| Non-Fucosylated Xyloglucan-5 | CCRC-M54 |
| | CCRC-M48 |
| | CCRC-M49 |
| | CCRC-M96 |
| | CCRC-M50 |
| | CCRC-M51 |
| | CCRC-M53 |
| Non-Fucosylated Xyloglucan-6 | CCRC-M57 |
| Fucosylated Xyloglucan | CCRC-M102 |
| | CCRC-M39 |
| | CCRC-M106 |
| | CCRC-M84 |
| | CCRC-M1 |
| Xylan-1/XG | CCRC-M111 |
| | CCRC-M108 |
| | CCRC-M109 |
| Xylan-2 | CCRC-M119 |
| | CCRC-M115 |
| | CCRC-M110 |
| | CCRC-M105 |
| Xylan-3 | CCRC-M117 |
| | CCRC-M113 |
| | CCRC-M120 |
| | CCRC-M118 |
| | CCRC-M116 |
| | CCRC-M114 |
| Xylan-4 | CCRC-M154 |
| | CCRC-M150 |
| Xylan-5 | CCRC-M144 |
| | CCRC-M146 |
| | CCRC-M145 |
| | CCRC-M155 |

TABLE 3-continued

Glycan Groups and Antibodies that Specifically Bind

| Glycan Group Recognized | mAb Names |
| --- | --- |
| Xylan-6 | CCRC-M153 |
| | CCRC-M151 |
| | CCRC-M148 |
| | CCRC-M140 |
| | CCRC-M139 |
| | CCRC-M138 |
| Xylan-7 | CCRC-M160 |
| | CCRC-M137 |
| | CCRC-M152 |
| | CCRC-M149 |
| Galactomannan-1 | CCRC-M75 |
| | CCRC-M70 |
| | CCRC-M74 |
| Galactomannan-2 | CCRC-M166 |
| | CCRC-M168 |
| | CCRC-M174 |
| | CCRC-M175 |
| Glucomannan | CCRC-M169 |
| | CCRC-M170 |
| β-Glucan | LAMP |
| | BG1 |
| HG Backbone-1 | CCRC-M131 |
| | CCRC-M38 |
| | JIM5 |
| HG Backbone-2 | JIM136 |
| | JIM7 |
| RG-I Backbone | CCRC-M69 |
| | CCRC-M35 |
| | CCRC-M36 |
| | CCRC-M14 |
| | CCRC-M129 |
| | CCRC-M72 |
| Linseed Mucilage RG-I | JIM3 |
| | CCRC-M40 |
| | CCRC-M161 |
| | CCRC-M164 |
| Physcomitrella Pectin | CCRC-M98 |
| | CCRC-M94 |
| RG-Ia | CCRC-M5 |
| | CCRC-M2 |
| RG-Ib | JIM137 |
| | JIM101 |
| | CCRC-M61 |
| | CCRC-M30 |
| RG-Ic | CCRC-M23 |
| | CCRC-M17 |
| | CCRC-M19 |
| | CCRC-M18 |
| | CCRC-M56 |
| | CCRC-M16 |
| RG-I/Arabinogalactan | CCRC-M60 |
| | CCRC-M41 |
| | CCRC-M80 |
| | CCRC-M79 |
| | CCRC-M44 |
| | CCRC-M33 |
| | CCRC-M32 |
| | CCRC-M13 |
| | CCRC-M42 |
| | CCRC-M24 |
| | CCRC-M12 |
| | CCRC-M7 |
| | CCRC-M77 |
| | CCRC-M25 |
| | CCRC-M9 |
| | CCRC-M128 |
| | CCRC-M126 |
| | CCRC-M134 |
| | CCRC-M125 |
| | CCRC-M123 |
| | CCRC-M122 |
| | CCRC-M121 |
| | CCRC-M112 |
| | CCRC-M21 |
| | JIM131 |
| | CCRC-M22 |

TABLE 3-continued

Glycan Groups and Antibodies that Specifically Bind

| Glycan Group Recognized | mAb Names |
|---|---|
| Arabinogalactan-1 | JIM132 |
| | JIM1 |
| | CCRC-M15 |
| | CCRC-M8 |
| | JIM16 |
| | JIM93 |
| | JIM94 |
| | JIM11 |
| | MAC204 |
| Arabinogalactan-2 | JIM20 |
| | JIM14 |
| | JIM19 |
| | JIM12 |
| | CCRC-M133 |
| Arabinogalactan-3 | CCRC-M107 |
| | JIM4 |
| | CCRC-M31 |
| | JIM17 |
| | CCRC-M26 |
| | JIM15 |
| | JIM8 |
| | CCRC-M85 |
| | CCRC-M81 |
| | MAC266 |
| Arabinogalactan-4 | PN 16.4B4 |
| | MAC207 |
| | JIM133 |
| | JIM13 |
| | CCRC-M92 |
| | CCRC-M91 |
| | CCRC-M78 |
| Unidentified | MAC265 |
| | CCRC-M97 |

What is claimed is:

1. A method for treating a biomass comprising polysaccharide and lignin, the method comprising:
   (i) providing a pre-treatment mixture comprising the biomass at a concentration of at least about 5% w/w, a single ionic liquid at a concentration of at least about 40% w/w, and optionally water, wherein the single ionic liquid is tetrabutylammonium hydroxide; and
   (ii) maintaining the mixture under pre-treatment conditions sufficient to dissolve at least a portion of the polysaccharide present in the biomass, wherein the pre-treatment conditions comprise a temperature of from about 35° C. to about 55° C. for a duration of from about 0.5 hours to about 3 hours, and maintaining the temperature of the pre-treatment mixture with less than about 40 MT/hr of steam to process 2000 MT/day of dry biomass.

2. The method of claim 1, wherein the pre-treatment conditions comprise conditions sufficient to remove at least 50% w/w of the lignin present in the biomass.

3. The method of claim 1, wherein the biomass is derived from switchgrass, pine, eucalyptus, or a combination thereof.

4. The method of claim 1, wherein the pH of the pre-treatment mixture is from about 7.5 to about 14.

5. The method of claim 1, wherein the single ionic liquid is at a concentration of between at least about 40% and about 90% w/w.

6. The method of claim 1, wherein providing the pre-treatment mixture comprises mechanically reducing the biomass to a smaller particle size.

7. The method of claim 1, wherein after (ii), the method further comprises:
   (iii) diluting the pre-treatment mixture with a polar solvent.

8. The method of claim 7, wherein the polar solvent is selected from the group consisting of water, methanol, ethanol, propanol, isopropanol, butanol, pentanol, hexanol, heptanol, octanol and isooctanol.

9. The method of claim 7, wherein the method comprises diluting the pre-treatment mixture with from about 2 volumes of polar solvent to about 10 volumes of polar solvent.

10. The method of claim 7, wherein:
    (a)
    step (iii) further comprises reducing the pH of the pre-treatment mixture with an acid, and after diluting the pre-treatment mixture, the method comprises:
    (iv) contacting the diluted pre-treated mixture with a glycoside hydrolase under conditions sufficient to hydrolyze at least a portion of glucan, thereby forming a sugar composition, wherein the sugar composition comprises at least one monosaccharide or oligosaccharide; or
    (b)
    wherein after diluting the pre-treatment mixture, the method comprises:
    (iv) collecting pre-treated biomass solids from the mixture, wherein the pre-treated biomass solids comprise at least about 50% w/w of glucan present in the biomass provided in the pre-treatment mixture, and wherein the method optionally further comprises
    (v) contacting the pre-treated biomass solids with a glycoside hydrolase under conditions sufficient to hydrolyze at least a portion of the glucan, thereby forming a sugar composition, wherein the sugar composition comprises at least one monosaccharide or oligosaccharide.

11. The method of claim 7, wherein after diluting the pre-treatment mixture, the method comprises:
    (iv) collecting pre-treated biomass solids from the mixture, wherein the pre-treated biomass solids comprise from about 90% w/w to about 95% w/w of glucan present in the biomass provided in the pre-treatment mixture.

12. The method of claim 10, wherein the glycoside hydrolase is selected from the group consisting of a cellulase, an endoglucanase, an exoglucanase, a β-glucosidase, a xylanase, and mixtures thereof.

13. A method for preparing a sugar composition comprising:
    (i) providing a pre-treatment mixture comprising biomass at a concentration of at least about 5% w/w, a single ionic liquid at a concentration of at least about 40% w/w, and optionally water, wherein the biomass comprises lignin and polysaccharide, and wherein the single ionic liquid is tetrabutylammonium hydroxide;
    (ii) maintaining the mixture under pre-treatment conditions sufficient to dissolve at least a portion of the polysaccharide present in the biomass, wherein the pre-treatment conditions comprise a temperature of from about 35° C. to about 55° C. for a duration of about 0.5 hours to about 3 hours, and maintaining the temperature of the pre-treatment mixture with less than about 40 MT/hr of steam to process 2000 MT/day of dry biomass;

(iii) diluting the pre-treatment mixture with a polar solvent to form a diluted pre-treatment mixture, and optionally collecting pre-treated biomass solids from the diluted pre-treatment mixture; and (iv) contacting the pre-treated biomass solids with a glycoside hydrolase under conditions sufficient to hydrolyze at least a portion of the polysaccharide, thereby forming a sugar composition, wherein the sugar composition comprises at least one monosaccharide or oligosaccharide, wherein the method optionally further comprises converting the sugar composition to a fermentation product, wherein the converting comprises fermenting a mixture containing the sugar composition of step (iv).

14. The method of claim 13, wherein the method comprises reducing the pH and the temperature of the diluted pre-treatment mixture and contacting the pre-treatment mixture with the glycoside hydrolase.

15. A method for converting a sugar composition to a fermentation product, the method comprising fermenting a mixture containing a sugar composition prepared according to the method of claim 10.

* * * * *